(12) United States Patent
Swiercz et al.

(10) Patent No.: US 7,592,422 B2
(45) Date of Patent: Sep. 22, 2009

(54) MODIFIED PLASMINOGEN ACTIVATOR INHIBITOR TYPE-1 AND METHODS BASED THEREON

(75) Inventors: Rafal Swiercz, Bastrop, TX (US); Steven H. Selman, Toledo, OH (US); Jerzy Jankun, Sylvania, OH (US); Joanna Chorostowska-Wynimko, Warsaw (PL); Ewa Skrzypczak-Jankun, Sylvania, OH (US)

(73) Assignee: Medical College of Ohio, Toledo, OH (US)

( * ) Notice: Subject to any disclaimer, the term of this patent is extended or adjusted under 35 U.S.C. 154(b) by 0 days.

(21) Appl. No.: 10/506,406

(22) PCT Filed: Mar. 4, 2003

(86) PCT No.: PCT/US03/06679

§ 371 (c)(1),
(2), (4) Date: Mar. 14, 2005

(87) PCT Pub. No.: WO03/080646

PCT Pub. Date: Oct. 2, 2003

(65) Prior Publication Data

US 2005/0158295 A1 Jul. 21, 2005

Related U.S. Application Data

(60) Provisional application No. 60/361,670, filed on Mar. 4, 2002.

(51) Int. Cl.
*C07K 1/00* (2006.01)
(52) U.S. Cl. .......................... 530/350; 530/300; 514/2; 514/12
(58) Field of Classification Search ................... None
See application file for complete search history.

(56) References Cited

U.S. PATENT DOCUMENTS 5,639,726 A 6/1997 Lawrence et al.
6,303,338 B1 10/2001 Ni et al.

FOREIGN PATENT DOCUMENTS

WO WO97/39028 10/1997

OTHER PUBLICATIONS

Wells, Biochemistry, vol. 29, pp. 8509-8517, 1990.*
Seffernick et al., J. Bacteriology, vol. 183, pp. 2405-2410, 2001.*
Schattauer, Thromb Haemosl, vol. 84, pp. 919-920, 2000.*
Xue et al. (Structure, vol. 6, No. 5, 1998).*
International Search Report dated Jan. 14, 2004 of corresponding PCT Application No. PCT/US03/06679.
Achbarou et al., Urokinase overproduction results in increased skeletal metastasis by prostate cancer cells in vivo. Cancer Res. May 1, 1994;54(9):2372-7.
Chorostowska-Wynimko et al., A Novel form of the plasminogen activator inhibitor created by cysteine mutations extends its half-life: relevance to cancer and angiogenesis. Mol Cancer Ther. Jan. 2003;2(1):19-28.
Conese et al., The urokinase/urokinase-receptor system and cancer invasion. Baillieres Clin Haematol. Jun. 1995;8(2):365-89.
Danø et al., Plasminogen activators, tissue degradation, and cancer. Adv Cancer Res. 1985;44:139-266.
Declerck et al., Measurement of plasminogen activator inhibitor 1 in biologic fluids with a murine monoclonal antibody-based enzyme-linked immunosorbent assay. Blood. Jan. 1988;71(1):220-5.
Declerck et al., Purification and characterization of a plasminogen activator inhibitor 1 binding protein from human plasma. Identification as a multimeric form of S protein (vitronectin). J Biol Chem. Oct. 25, 1988;263(30):15454-61.
Ellis et al. Plasminogen activation by receptor-bound urokinase. Semin Thromb Hemost. Jul. 1991;17(3):194-200.
Festuccia et al., Plasminogen activator activities in short-term tissue cultures of benign prostatic hyperplasia and prostatic carcinoma. Oncol Res. 1995;7(3-4):131-8.
Hajjar et al., Identification and characterization of human endothelial cell membrane binding sites for tissue plasminogen activator and urokinase. J Biol Chem. Feb. 15, 1990;265(5):2908-16.
Hekman et al., Bovine plasminogen activator inhibitor 1: specificity determinations and comparison of the active, latent, and guanidine-activated forms. Biochemistry. Apr. 19, 1988;27(8):2911-8.
Hekman et al. Endothelial cells produce a latent inhibitor of plasminogen activators that can be activated by denaturants. J Biol Chem. Sep. 25, 1985;260(21):11581-7.
Hoylaerts et al., Kinetics of the activation of plasminogen by human tissue plasminogen activator. Role of fibrin. J Biol Chem. Mar. 25, 1982;257(6):2912-9.
Hsueh et al., Molecular mechanisms in the hormonal regulation of plasminogen activator activity in ovarian granulosa cells and cumulus-oocyte complexes. Prog Clin Biol Res. 1988;267:227-57.

(Continued)

*Primary Examiner*—Hope A Robinson
(74) *Attorney, Agent, or Firm*—Frommer Lawrence & Haug LLP

(57) ABSTRACT

The present invention is based upon the discovery that modified plasminogen activator inhibitor type-I (PAI-1) in which two or more amino acid residues that do not contain a sulfhydryl group have been replaced with amino acid residues that contain a sulfhydryl group and, therefore, forms intramolecular disulfide bonds, have increased in vivo half-life. Also disclosed are the modified PAI-1 proteins, derivatives and analogs thereof, specific antibodies, nucleic acid molecules and host cells. Methods for producing modified PAI-1, derivatives and analogs are also provided. The invention further relates to Therapeutics, pharmaceutical compositions and method of using the composition for treatment. The invention may be used to inhibit angiogenesis in a subject, thereby treating diseases or conditions associated with undesired angiogenesis and cell proliferation. Such conditions include psoriasis, chronic inflammation, tumor invasion and metastasis and conditions in which angiogenesis is pathogenic. The modifide PAI-1 molecules of the present invention are useful for the treatment, prophylaxis, management and amelioration of cardiovascular diseases such as, but not limited to those that are related to hyperfibrinolysis, hemophilia, and vessel leakage syndrome.

20 Claims, 16 Drawing Sheets

OTHER PUBLICATIONS

Figure 3:
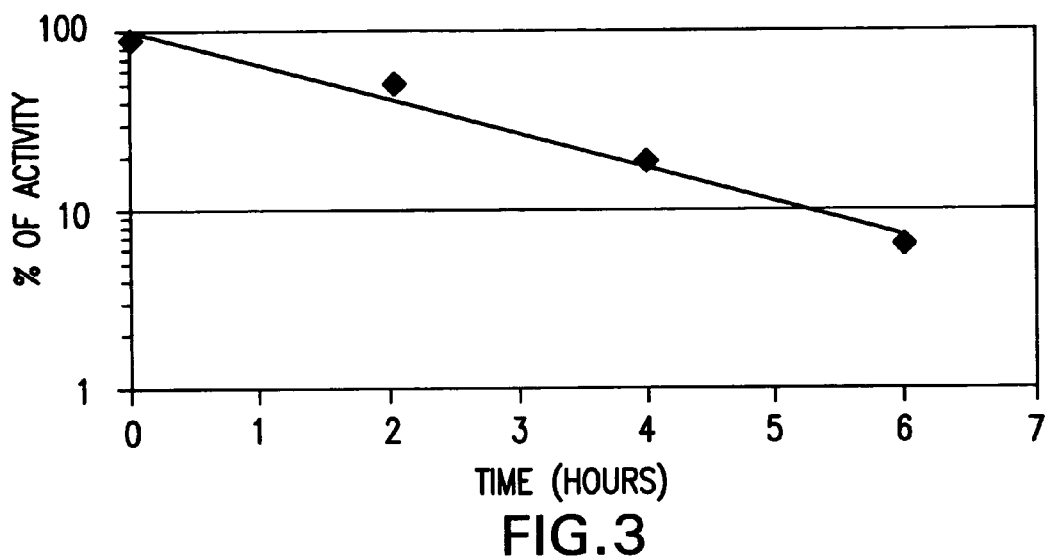

Jankun et al., Expression and localization of elements of the plasminogen activation system in benign breast disease and breast cancers. J Cell Biochem. Oct. 1993;53(2):135-44.

Jankun et al., Inhibitors of urokinase reduce size of prostate cancer xenografts in sever combined immunodeficient mice. Cancer Res. Feb. 15, 1997;57(4):559-63. Erratum in: Cancer Res Jan. 1, 1998;58(1):179.

Jankun et al., Malignant transformation of human fibroblasts correlates with increased activity of receptor-bound plasminogen activator. Cancer Res. Feb. 15, 1991;51(4):1221-6.

Kwaan et al., Components of the plasminogen-plasmin system in human tumor cell lines. Semin Thromb Hemost. Jul 1991;17(3):175-82.

Lawrence et al., Engineering plasminogen activator inhibitor I mutants with increased functional stability. Biochemistry. Mar. 29, 1994;33(12):3643-8.

Lawrence et al., Plasminogen activator inhibitors in Molecular Basis of Thrombosis and Hemostasis. Marcel Dekker, Inc., High et al., eds. 1995;25:517-43

Lawrence et al., Purification of active human plasminogen activator inhibitor I from *Escherichia coli*. Comparison with natural and recombinant forms purified from eucaryotic cells. Eur J Biochem. Dec. 22, 1989;186(3):523-33.

Levin et al., Conversion of the active to latent plasminogen activator inhbitor from human endothelial cells. Blood. Oct. 1987;70(4):1090-8.

Mayer, Biochemical and biological aspects of the plasminogen activation system. Clin Biochem. Jun. 1990;23(3):197-211.

Mayer, The pharmacokinetics of plasminogen activator inhibitor-1 in the rabbit. Blood. Oct. 15, 1990;76(8):1514-20.

Mimuro et al., Binding of type 1 plasminogen activator inhibitor to the extracellular matrix of cultured bovine endothelial cells. J Biol Chem. Mar. 25, 1989;264(9):5058-63.

Mimuro et al., Extracellular matrix of cultured bovine aortic endothelial cells contains functionally active type 1 plasminogen activator inhibitor. Blood. Sep. 1987;70(3):721-8.

Moscatelli et al., Membrane and matrix localization of proteinases: a common theme in tumor cell invasion and angiogenesis. Biochim Biophys Acta. Aug. 3, 1988;948(1):67-85.

Ossowski, In vivo invasion of modified chorioallantoic membrane by tumor cells: the role of cell surface-bound urokinase. J Cell Biol. Dec. 1988;107(6 Pt 1):2437-45.

Pepper et al., Urokinase-type plasminogen activator is induced in migrating capillary endothelial cells. J Cell Biol. Dec. 1987;105(6 Pt 1):2535-41.

Pepper et al., Upregulation of urokinase receptor expression on migrating endothelial cells. J Cell Biol. Aug. 1993;122(3):673-84.

Plow et al., Cellular regualtion of fibrinolysis. Thromb Haemost. Jul. 12, 1991;66(1):32-6.

Pöllänen et al., Directed plasminogen activation at the surface of normal and malignant cells. Adv Cancer Res. 1991;57:273-328.

Rånby et al., A sensitive assay for tissue plasminogen activator. Thromb Res. Sep. 15, 1982;27(6):743-9.

Saksela et al., Cell-associated plasminogen activation: regulation and physiological functions. Annu Rev Cell Biol. 1988;4:93-126.

Saksela, Plasminogen activation and regulation of pericellular proteolysis. Biochim Biophys Acta. Nov. 12, 1985;823(1):35-65.

Seetharam et al., Purification and characterization of active and latent forms of recombinant plasminogen activator inhibitor 1 produced in *Escherichia coli*. Biochemistry. Oct. 20, 1992;31(41):9877-82.

Swiercz et al., Angiostatic activity of synthetic inhibitors of urokinase type plasminogen activator. Oncol Rep. May-Jun. 1999;6(3):523-6.

van Mourik et al., Purification of an inhibitor of plasminogen activator (antiactivator) synthesized by endothelial cells. J Biol Chem. Dec. 10, 1984;259(23):14914-21.

Vaughan et al., Studies of recombinant plasminogen activator inhibitor-I in rabbits. Pharmacokinetics and evidence for reactivation of latent plasminogen activator inhibitor-I in vivo. Circd Res. Nov. 1990;67(5):1281-6.

Wilson et al., Plasminogen activator and metalloprotease activities of Du-145, PC-3, and I-LN-PC-3-1A human prostate tumors grown in nude mice: correlation with tumor invasive behavior. Cell Mol Biol Res. 1993;39(8):751-60.

Wiman et al., Inactivation of tissue plasminogen activator in plasma. Demonstration of a complex with a new rapid inhibitor. J Biol Chem. Mar. 25, 1984;259(6):3644-7.

Wiman et al., Plasminogen activator release during venous stasis and exercise as determined by a new specific assay. Clin Chim Acta. Jan. 24, 1983;127(2):279-88.

Wiman et al., The role of the fibrinolytic system in deep vein thrombosis. J Lab Clin Med. Feb. 1985;105(2):265-70.

Wun et al., Affinity purification of active plasminogen activator inhibitor-1 (PAI-1) using immobilized anhydrourokinase. Demonstration of the binding, stabilization, and activation of PAI-1 by vitronectin. J. Biol Chem. May 15, 1989;264(14):7862-8.

Chorostowska-Wynimko et al., 2002, "Cysteine mutations of plasminogen activator inhibitory type I extend its half-life. Implication for inhibition of cancer angiogenesis." Proc. Amer. Associat. For Can. Res. Ann. Meeting. 43:141.

Im Hana et al., 2000, "Bypassing the kinetic trap of serpin protein folding by loop extension," Protein Sci. 9(8): 1497-1502.

Simonovic et al., 2000, "The native metastable fold of C1-inhibitor is stabilized by disulfide bonds." Biochimica et Biophysica Acta. 1481(1): 97-102.

Tucker et al., 1995, "Engineering of plasminogen activator inhibitor-1 to reduce the rate of latency transition," Nat. Struct. Biol. 2(6): 442-445.

* cited by examiner

```
            GAATTCCTGCAGCTCAGCAGCCGCCGCCAGAGCAGGACGAACCGCCAATCGCAAGGCACC
         1  ----------+---------+---------+---------+---------+---------+ 60
            CTTAAGGACGTCGAGTCGTCGGCGGCGGTCTCGTCCTGCTTGGCGGTTAGCGTTCCGTGG

TCTGAGAACTTCAGGATGCAGATGTCTCCAGCCCTCACCTGCCTAGTCCTGGGCCTGGCC
        61  ----------+---------+---------+---------+---------+---------+ 120
            AGACTCTTGAAGTCCTACGTCTACAGAGGTCGGGAGTGGACGGATCAGGACCCGGACCGG
  aa                      M  Q  M  S  P  A  L  T  C  L  V  L  G  L  A
                          |Signal Peptide
            CTTGTCTTTGGTGAAGGGTCTGCTGTGCACCATCCCCCATCCTACGTGGCCCACCTGGCC
       121  ----------+---------+---------+---------+---------+---------+ 180
            GAACAGAAACCACTTCCCAGACGACACGTGGTAGGGGGTAGGATGCACCGGGTGGACCGG
  aa         L  V  F  G  E  G  S  A |V  H  H  P  P  S  Y  V  A  H  L  A  12
                                      Start Mature Protein
            TCAGACTTCGGGGTGAGGGTGTTTCAGCAGGTGGCGCAGGCCTCCAAGGACCGCAACGTG
       181  ----------+---------+---------+---------+---------+---------+ 240
            AGTCTGAAGCCCCACTCCCACAAAGTCGTCCACCGCGTCCGGAGGTTCCTGGCGTTGCAC
  aa         S  D  F  G  V  R  V  F  Q  Q  V  A  Q  A  S  K  D  R  N  V  32

GTTTTCTCACCCTATGGGGTGGCCTCGGTGTTGGCCATGCTCCAGCTGACAACAGGAGGA
       241  ----------+---------+---------+---------+---------+---------+ 300
            CAAAAGAGTGGGATACCCCACCGGAGCCACAACCGGTACGAGGTCGACTGTTGTCCTCCT
  aa         V  F  S  P  Y  G  V  A  S  V  L  A  M  L  Q  L  T  T  G  G  52

GAAACCCAGCAGCAGATTCAAGCAGCTATGGGATTCAAGATTGATGACAAGGGCATGGCC
       301  ----------+---------+---------+---------+---------+---------+ 360
            CTTTGGGTCGTCGTCTAAGTTCGTCGATACCCTAAGTTCTAACTACTGTTCCCGTACCGG
  aa         E  T  Q  Q  Q  I  Q  A  A  M  G  F  K  I  D  D  K  G  M  A  72

CCCGCCCTCCGGCATCTGTACAAGGAGCTCATGGGGCCATGGAACAAGGATGAGATCAGC
       361  ----------+---------+---------+---------+---------+---------+ 420
            GGGCGGGAGGCCGTAGACATGTTCCTCGAGTACCCCGGTACCTTGTTCCTACTCTAGTCG
  aa         P  A  L  R  H  L  Y  K  E  L  M  G  P  W  N  K  D  E  I  S  92

ACCACAGACGCGATCTTCGTCCAGCGGGATCTGAAGCTGGTCCAGGGCTTCATGCCCCAC
       421  ----------+---------+---------+---------+---------+---------+ 480
            TGGTGTCTGCGCTAGAAGCAGGTCGCCCTAGACTTCGACCAGGTCCCGAAGTACGGGGTG
  aa         T  T  D  A  I  F  V  Q  R  D  L  K  L  V  Q  G  F  M  P  H  112

TTCTTCAGGCTGTTCCGGAGCACGGTCAAGCAAGTGGACTTTTCAGAGGTGGAGAGAGCC
       481  ----------+---------+---------+---------+---------+---------+ 540
            AAGAAGTCCGACAAGGCCTCGTGCCAGTTCGTTCACCTGAAAAGTCTCCACCTCTCTCGG
  aa         F  F  R  L  F  R  S  T  V  K  Q  V  D  F  S  E  V  E  R  A  132
```

FIG.1A

```
                AGATTCATCATCAATGACTGGGTGAAGACACACACAAAAGGTATGATCAGCAACTTGCTT
        541     ---------+---------+---------+---------+---------+---------+ 600
                TCTAAGTAGTAGTTACTGACCCACTTCTGTGTGTGTTTTCCATACTAGTCGTTGAACGAA
aa              R   F   I   I   N   D   W   V   K   T   H   T   K   G   M   I   S   N   L   L   152

GGGAAAGGAGCCGTGGACCAGCTGACACGGCTGGTGCTGGTGAATGCCCTCTACTTCAAC
        601     ---------+---------+---------+---------+---------+---------+ 660
                CCCTTTCCTCGGCACCTGGTCGACTGTGCCGACCACGACCACTTACGGGAGATGAAGTTG
aa              G   K   G   A   V   D   Q   L   T   R   L   V   L   V   N   A   L   Y   F   N   172

GGCCAGTGGAAGACTCCCTTCCCCGACTCCAGCACCCACCGCCGCCTCTTCCACAAATCA
        661     ---------+---------+---------+---------+---------+---------+ 720
                CCGGTCACCTTCTGAGGGAAGGGGCTGAGGTCGTGGGTGGCGGCGGAGAAGGTGTTTAGT
aa              G   Q   W   K   T   P   F   P   D   S   S   T   H   R   R   L   F   H   K   S   192

GACGGCAGCACTGTCTCTGTGCCCATGATGGCTCAGACCAACAAGTTCAACTATACTGAG
        721     ---------+---------+---------+---------+---------+---------+ 780
                CTGCCGTCGTGACAGAGACACGGGTACTACCGAGTCTGGTTGTTCAAGTTGATATGACTC
aa              D   G   S   T   V   S   V   P   M   M   A   Q   T   N   K   F   N   Y   T   E   212

TTCACCACGCCCGATGGCCATTACTACGACATCCTGGAACTGCCCTACCACGGGGACACC
        781     ---------+---------+---------+---------+---------+---------+ 840
                AAGTGGTGCGGGCTACCGGTAATGATGCTGTAGGACCTTGACGGGATGGTGCCCCTGTGG
aa              F   T   T   P   D   G   H   Y   Y   D   I   L   E   L   P   Y   H   G   D   T   232

CTCAGCATGTTCATTGCTGCCCCTTATGAAAAAGAGGTGCCTCTCTCTGCCCTCACCAAC
        841     ---------+---------+---------+---------+---------+---------+ 900
                GAGTCGTACAAGTAACGACGGGGAATACTTTTTCTCCACGGAGAGAGACGGGAGTGGTTG
aa              L   S   M   F   I   A   A   P   Y   E   K   E   V   P   L   S   A   L   T   N   252

ATTCTGAGTGCCCAGCTCATCAGCCACTGGAAAGGCAACATGACCAGGCTGCCCCGCCTC
        901     ---------+---------+---------+---------+---------+---------+ 960
                TAAGACTCACGGGTCGAGTAGTCGGTGACCTTTCCGTTGTACTGGTCCGACGGGGCGGAG
aa              I   L   S   A   Q   L   I   S   H   W   K   G   N   M   T   R   L   P   R   L   272

CTGGTTCTGCCCAAGTTCTCCCTGGAGACTGAAGTCGACCTCAGGAAGCCCCTAGAGAAC
        961     ---------+---------+---------+---------+---------+---------+ 1020
                GACCAAGACGGGTTCAAGAGGGACCTCTGACTTCAGCTGGAGTCCTTCGGGGATCTCTTG
aa              L   V   L   P   K   F   S   L   E   T   E   V   D   L   R   K   P   L   E   N   292

CTGGGAATGACCGACATGTTCAGACAGTTTCAGGCTGACTTCACGAGTCTTTCAGACCAA
        1021    ---------+---------+---------+---------+---------+---------+ 1080
                GACCCTTACTGGCTGTACAAGTCTGTCAAAGTCCGACTGAAGTGCTCAGAAAGTCTGGTT
aa              L   G   M   T   D   M   F   R   Q   F   Q   A   D   F   T   S   L   S   D   Q   312
```

FIG.1B

```
            GAGCCTCTCCACGTCGCGCAGGCGCTGCAGAAAGTGAAGATCGAGGTGAACGAGAGTGGC
      1081  ---------+---------+---------+---------+---------+---------+ 1140
            CTCGGAGAGGTGCAGCGCGTCCGCGACGTCTTTCACTTCTAGCTCCACTTGCTCTCACCG
aa           E  P  L  H  V  A  Q  A  L  Q  K  V  K  I  E  V  N  E  S  G  332

ACGGTGGCCTCCTCATCCACAGCTGTCATAGTCTCAGCCCGCATGGCCCCCGAGGAGATC
      1141  ---------+---------+---------+---------+---------+---------+ 1200
            TGCCACCGGAGGAGTAGGTGTCGACAGTATCAGAGTCGGGCGTACCGGGGGCTCCTCTAG
aa           T  V  A  S  S  S  T  A  V  I  V  S  A  R  M  A  P  E  E  I  352

ATCATGGACAGACCCTTCCTCTTTGTGGTCCGGCACAACCCCACAGGAACAGTCCTTTTC
      1201  ---------+---------+---------+---------+---------+---------+ 1260
            TAGTACCTGTCTGGGAAGGAGAAACACCAGGCCGTGTTGGGGTGTCCTTGTCAGGAAAAG
aa           I  M  D  R  P  F  L  F  V  V  R  H  N  P  T  G  T  V  L  F  352

ATGGGCCAAGTGATGGAACCCTGACCCTGGGGAAAGACGCCTTCATCTGGGACAAAACTG
      1261  ---------+---------+---------+---------+---------+---------+ 1320
            TACCCGGTTCACTACCTTGGGACTGGGACCCCTTTCTGCGGAAGTAGACCCTGTTTTGAC
aa           M  G  Q  V  M  E  P  *  379

GAGATGCATCGGGAAAGAAGAAACTCCGAAGAAAAGAATTTTAGTGTTAATGACTCTTTC
      1321  ---------+---------+---------+---------+---------+---------+ 1380
            CTCTACGTAGCCCTTTCTTCTTTGAGGCTTCTTTTCTTAAAATCACAATTACTGAGAAAG

TGAAGGAAGAGAAGACATTTGCCTTTTGTTAAAAGATGGTAAACCAGATCTGTCTCCAAG
      1381  ---------+---------+---------+---------+---------+---------+ 1440
            ACTTCCTTCTCTTCTGTAAACGGAAAACAATTTTCTACCATTTGGTCTAGACAGAGGTTC

ACCTTGGCCTCTCCTTGGAGGACCTTTAGGTCAAACTCCCTAGTCTCCACCTGAGACCCT
      1441  ---------+---------+---------+---------+---------+---------+ 1500
            TGGAACCGGAGAGGAACCTCCTGGAAATCCAGTTTGAGGGATCAGAGGTGGACTCTGGGA

GGGAGAGAAGTTTGAAGCACAACTCCCTTAAGGTCTCCAAACCAGACGGTGACGCCTGCG
      1501  ---------+---------+---------+---------+---------+---------+ 1560
            CCCTCTCTTCAAACTTCGTGTTGAGGGAATTCCAGAGGTTTGGTCTGCCACTGCGGACGC

GGACCATCTGGGGCACCTGCTTCCACCCGTCTCTCTGCCCACTCGGGTCTGCAGACCTGG
      1561  ---------+---------+---------+---------+---------+---------+ 1620
            CCTGGTAGACCCCGTGGACGAAGGTGGGCAGAGAGACGGGTGAGCCCAGACGTCTGGACC

1621  TTCCCACTGAGGCCCTTTGCAGGATGGAACTACGGGGCTTACAGGAGCTTTTGTGTGCCT
            ---------+---------+---------+---------+---------+---------+ 1680
            AAGGGTGACTCCGGGAAACGTCCTACCTTGATGCCCCGAATGTCCTCGAAAACACACGGA
```

FIG. 1C

```
1681  GGTAGAAACTATTTCTGTTCCAGTCACATTGCCATCACTCTTGTACTGCCTGCCACCGCG
      ---------+---------+---------+---------+---------+---------+ 1740
      CCATCTTTGATAAAGACAAGGTCAGTGTAACGGTAGTGAGAACATGACGGACGGTGGCGC

GAGGAGGCTGGTGACAGGCCAAAGGCCAGTGGAAGAAACACCCTTTCATCTCAGAGTCCA
1741  ---------+---------+---------+---------+---------+---------+ 1800
      CTCCTCCGACCACTGTCCGGTTTCCGGTCACCTTCTTTGTGGGAAAGTAGAGTCTCAGGT

CTGTGGCACTGGCCACCCCTCCCCAGTACAGGGGTGCTGCAGGTGGCAGAGTGAATGTCC
1801  ---------+---------+---------+---------+---------+---------+ 1860
      GACACCGTGACCGGTGGGGAGGGGTCATGTCCCCACGACGTCCACCGTCTCACTTACAGG

CCCATCATGTGGCCCAACTCTCCTGGCCTGGCCATCTCCCTCCCCAGAAACAGTGTGCAT
1861  ---------+---------+---------+---------+---------+---------+ 1920
      GGGTAGTACACCGGGTTGAGAGGACCGGACCGGTAGAGGGAGGGGTCTTTGTCACACGTA

GGGTTATTTTGGAGTGTAGGTGACTTGTTTACTCATTGAAGCAGATTTCTGCTTCCTTTT
1921  ---------+---------+---------+---------+---------+---------+ 1980
      CCCAATAAAACCTCACATCCACTGAACAAATGAGTAACTTCGTCTAAAGACGAAGGAAAA

ATTTTTATAGGAATAGAGGAAGAAATGTCAGATGCGTGCCCAGCTCTTCACCCCCCAATC
1981  ---------+---------+---------+---------+---------+---------+ 2040
      TAAAAATATCCTTATCTCCTTCTTTACAGTCTACGCACGGGTCGAGAAGTGGGGGGTTAG

TCTTGGTGGGGAGGGGTGTACCTAAATATTTATCATATCCTTGCCCTTGAGTGCTTGTTA
2041  ---------+---------+---------+---------+---------+---------+ 2100
      AGAACCACCCCTCCCCACATGGATTTATAAATAGTATAGGAACGGGAACTCACGAACAAT

GAGAGAAAGAGAACTACTAAGGAAAATAATATTATTTAAACTCGCTCCTAGTGTTTCTTT
2101  ---------+---------+---------+---------+---------+---------+ 2160
      CTCTCTTTCTCTTGATGATTCCTTTTATTATAATAAATTTGAGCGAGGATCACAAAGAAA

GTGGTCTGTGTCACCGTATCTCAGGAAGTCCAGCCACTTGACTGGCACACACCCCTCCGG
2161  ---------+---------+---------+---------+---------+---------+ 2220
      CACCAGACACAGTGGCATAGAGTCCTTCAGGTCGGTGAACTGACCGTGTGTGGGGAGGCC

ACATCCAGCGTGACGGAGCCCACACTGCCACCTTGTGGCCGCCTGAGACCCTCGCGCCCC
2221  ---------+---------+---------+---------+---------+---------+ 2280
      TGTAGGTCGCACTGCCTCGGGTGTGACGGTGGAACACCGGCGGACTCTGGGAGCGCGGGG

CCGCGCCCCCCGCGCCCCTCTTTTTTCCCCTTGATGGAAATTGACCATACAATTTCATCCT
2281  ---------+---------+---------+---------+---------+---------+ 2340
      GGCGCGGGGGGCGCGGGGAGAAAAAGGGGAACTACCTTTAACTGGTATGTTAAAGTAGGA
```

FIG. 1D

```
           CCTTCAGGGGATCAAAAGGACGGAGTGGGGGGACAGAGACTCAGATGAGGACAGAGTGGT
2341       ---------+---------+---------+---------+---------+---------+ 2400
           GGAAGTCCCCTAGTTTTCCTGCCTCACCCCCCTGTCTCTGAGTCTACTCCTGTCTCACCA

TTCCAATGTGTTCAATAGATTTAGGAGCAGAAATGCAAGGGGCTGCATGACCTACCAGGA
2401       ---------+---------+---------+---------+---------+---------+ 2460
           AAGGTTACACAAGTTATCTAAATCCTCGTCTTTACGTTCCCCGACGTACTGGATGGTCCT

CAGAACTTTCCCCAATTACAGGGTGACTCACAGCCGCATTGGTGACTCACTTCAATGTGT
2461       ---------+---------+---------+---------+---------+---------+ 2520
           GTCTTGAAAGGGGTTAATGTCCCACTGAGTGTCGGCGTAACCACTGAGTGAAGTTACACA

CATTTCCGGCTGCTGTGTGTGAGCAGTGGACACGTGAGGGGGGGGTGGGTGAGAGAGACA
2521       ---------+---------+---------+---------+---------+---------+ 2580
           GTAAAGGCCGACGACACACACTCGTCACCTGTGCACTCCCCCCCCACCCACTCTCTCTGT

GGCAGCTCGGATTCAACTACCTTAGATAATATTTCTGAAAACCTACCAGCCAGAGGGTAG
2581       ---------+---------+---------+---------+---------+---------+ 2640
           CCGTCGAGCCTAAGTTGATGGAATCTATTATAAAGACTTTTGGATGGTCGGTCTCCCATC

GGCACAAAGATGGATGTAATGCACTTTGGGAGGCCAAGGCGGGAGGATTGCTTGAGCCCA
2641       ---------+---------+---------+---------+---------+---------+ 2700
           CCGTGTTTCTACCTACATTACGTGAAACCCTCCGGTTCCGCCCTCCTAACGAACTCGGGT

GGAGTTCAAGACCAGCCTGGGCAACATACCAAGACCCCCGTCTCTTTAAAAATATATATA
2701       ---------+---------+---------+---------+---------+---------+ 2760
           CCTCAAGTTCTGGTCGGACCCGTTGTATGGTTCTGGGGGCAGAGAAATTTTTATATATAT

TTTTAAATATACTTAAATATATATTTCTAATATCTTTAAATATATATATATATTTTAAAG
2761       ---------+---------+---------+---------+---------+---------+ 2820
           AAAATTTATATGAATTTATATATAAAGATTATAGAAATTTATATATATATATAAAATTTC

ACCAATTTATGGGAGAATTGCACACAGATGTGAAATGAATGTAATCTAATAGAAGC
2821       ---------+---------+---------+---------+------ 2876
           TGGTTAAATACCCTCTTAACGTGTGTCTACACTTTACTTACATTAGATTATCTTCG
```

FIG. 1E

MQMSPALTCLVLGLALVFGEGSA
Signal Peptide

VHHPPSYVAHLASDFGVRVFQQVAQASKDRNVVFSPYGVASVLAMLQLTTGGETQQQIQA

AMGFKIDDKGMAPALRHLYKELMGPWNKDEISTTDAIFVQRDLKLVQGFMPHFFRLFRST

VKQVDFSEVERARFIINDWVKTHTKGMISNLLGKGAVDQLTRLVLVNALYFNGQWKTPFP

DSSTHRRLFHKSDGSTVSVPMMAQTNKFNYTEFTTPDGHYYDILELPYHGDTLSMFIAAP

YEKEVPLSALTNILSAQLISHWKGNMTRLPRLLVLPKFSLETEVDLRKPLENLGMTDMFR

QFQADFTSLSDQEPLHVAQALQKVKIEVNESGTVASSSTAVIVSARMAPEEIIMDRPFLF

VVRHNPTGTVLFMGQVMEP

FIG.2A

```
          10        20        30        40        50        60
          |         |         |         |         |         |
VHHPPSYVAHLASDFGVRVFQQVAQASKDRNVVFSPYGVASVLAMLQLTTGGETQQQIQA 70        80        90       100       110       120
          |         |         |         |         |         |
AMGFKIDDKGMAPALRHLYKELMGPWNKDEISTTDAIFVQRDLKLVQGFMPHFFRLFRST 130       140       150       160       170       180
          |         |         |         |         |         |
VKQVDFSEVERARFIINDWVKTHTKGMISNLLGKGAVDQLTRLVLVNALYFNGQWKTPFP 190       200       210       220       230       240
          |         |         |         |         |         |
DSSTHRRLFHKSDGSTVSVPMMAQTNKFNYTEFTTPDGHYYDILELPYHGDTLSMFIAAP 250       260       270       280       290       300
          |         |         |         |         |         |
YEKEVPLSALTNILSAQLISHWKGNMTRLPRLLVLPKFSLETEVDLRKPLENLGMTDMFR 310       320       330       340       350       360
          |         |         |         |         |         |
QFQADFTSLSDQEPLHVAQALQKVKIEVNESGTVASSSTAVIVSARMAPEEIIMDRPFLF

370
          |
VVRHNPTGTVLFMGQVMEP
```

FIG.2B

US 7,592,422 B2

MODIFIED PLASMINOGEN ACTIVATOR INHIBITOR TYPE-1 AND METHODS BASED THEREON

This application claims priority to PCT Application No. PCT/US03/06679, filed Mar. 4, 2003 and U.S. Provisional Patent Application Ser. No. 60/361,670, filed Mar. 4, 2002, which are incorporated herein by reference in their entireties.

The invention was made with Government support under Department of Defense DAMD 17-01-1-0553. The government has certain rights in the invention.

1. FIELD OF THE INVENTION

The present invention relates to modified plasminogen activator inhibitor type-1 (PAI-1), and derivatives and analogs thereof, in which two or more amino acid residues that do not contain a sulfhydryl group have been replaced with amino acid residues that contain a sulfhydryl group so that intramolecular disulfide bonds can be formed. These modified PAI-1 molecules, and derivatives and analogs thereof, have increased in vivo half-life of the active form of PAI-1. Also disclosed are peptides of such modified proteins, antibodies that specifically bind the PAI-1 molecules, derivatives and analogs thereof, nucleic acid molecules, particularly DNA, encoding the modified proteins, and host cells containing such nucleic acids. Methods for producing modified PAI-1, and derivatives and analogs thereof, are also provided. The invention flier relates to pharmaceutical compositions comprising modified PAI-1 molecules of the invention and methods of using these pharmaceutical compositions for treatment. The invention may be used to inhibit angiogenesis in a subject, thereby treating diseases or conditions associated with undesired angiogenesis, and also provides methods to inhibit cell proliferation. Such conditions include psoriasis, chronic inflammation, rheumatoid arthritis, inflammatory bowel disease, asthmas, and other inflammatory conditions, tumor invasion, primary and metastatic neoplastic diseases (e.g., cancer), and other conditions in which cell proliferation and/or angiogenesis is pathogenic. The invention may also be used to treat cardiovascular diseases such as, but not limited to those that are related to hyperfibrinolysis, hemophilia, and vessel leakage syndrome.

2. BACKGROUND OF THE INVENTION

Metastasis is the cause of most cancer-related deaths. The proteolytic degradation of the extracellular matrix is recognized as a mechanism that plays an important role in the metastatic process. Proteolytic enzymes are required to mediate tumor cell invasion into adjacent tissues and initiate the metastatic process. Urokinase plasminogen activator (uPA) is commonly overexpressed by many different human cancers. Conese et al., 1995, Clinical Hematology 8(2):365-389.

The uPA system contains the following elements: (i) Plasminogen—a non-active enzyme that is cleaved to form the active plasmin. Plasmin is a strong proteolytic enzyme able to digest proteins of connective tissue and basement membranes. Plasmin can activate other latent proteolytic enzymes, thus broadening the spectrum of proteins degraded. Pro-collagenase is activated to collagenase in this way. Plasmin is a key enzyme in tissue remodeling, tumor invasion and development of distant metastasis. (ii) Activators—uPA and tissue plasminogen activator (tPA). Both are weak proteolytic enzymes that activate plasminogen to plasmin by proteolytic cleavage. uPA is involved in pericellular proteolysis during cell migration, wound healing, and tissue remodeling under a variety of physiological and pathological conditions. tPA mainly mediates intravascular thrombolysis (Conese et al., 1995, Clin. Hema. 8(2):365-389; Ossowski et al., 1988, J. Cell Biol 107:2437-2445; Jankun et al., 1999, Onco. Rep. 6:523-526). (iii) Inhibitors of plasminogen activators. There are four proteins known for their inhibitory activity toward uPA: PAI-1, PAI-2, PAI-3 and a protein called nexin. (iv) uPAR, a uPA receptor is a glycoprotein that binds uPA to the cell surface. Surface bound uPA retains its ability to activate plasminogen. High numbers of uPA receptors on the surface of cancer cells, if occupied by uPA, create elevated proteolytic activity in the proximity of cancer cells and hence allow dissolution of surrounding tissue which facilitate cancer invasion. Kwaan et al., 1991, Sem. Throm. Hemo. 17:175-182.

2.1. Plasminogen Activators

Plasminogen activators (PAs) are specific serine proteinases that activate the proenzyme plasminogen, by cleavage of a single Arg-Val peptide bond, to the enzyme plasmin (Saksela O, Biochim Biophys Acta (1985) 823:35-65). Two plasminogen activators are found in mammals, tissue-type PA (tPA) and urokinase-type PA (uPA) (Saksela O et al, Annu Rev Cell Biol (1988) 4:93-126). These enzymes are thought to influence critically many biological processes, including vascular fibrinolysis (Bachmann E, Thromb Haemost (1987) 10:227-265), ovulation (Hsuch A J W et al, in Haseltine F P et al, eds, Meiotic Inhibition: Molecular Control of Meiosis: 1988:227-258. New York. Liss), inflammation (Pollanen J et al., Adv Cancer Res (1991) 57:273-328), tumor metastasis (Dano K et al., Adv Cancer Res (1985) 44:139-266), angiogenesis (Moscatelli D et al., Biochim Biophys Acta (1988) 948:67-85), and tissue remodeling (Saksela, supra).

The regulation of PAs is a complex process controlled on many levels. The synthesis and release of PAs are governed by various hormones, growth factors, and cytokines (Saksela, supra; Dano et al., supra). Following secretion, PA activity can be regulated both positively and negatively by a number of specific protein-protein interactions. Activity can be enhanced or concentrated by interactions with fibrin (Hoylaerts M et al., J Biol Chem, 1982, 257:2912-2919), the uPA receptor (uPAR)(Ellis V et al., Semin Thromb Hemost, 1991, 17:194-200), the tPA receptor (tPAR) (Hajjar K A et al., 1990, J Biol Chem, 265:2908-2916), or the plasminogen receptor (Plow E F et al., 1991, Thromb Haemost 66:32-36).

PA activity can be downregulated by specific PA inhibitors (PAIs) (Lawrence, D. A et al., In: Molecular Biology of Thrombosis and Hemostasis, Roberts, H. R. et al., (Eds.), Marcel Dekker Inc., New York, chapter 25, pp. 517-543 (1995)). In addition, PA activity is dependent on its location or microenvironment and may be different in solution (e.g., circulating blood) as compared to a solid-phase (e.g., on a cell surface or in the extracellular matrix (ECM)). The overall activity of the PA system is determined by the interactions among these various elements and the balance between the opposing activities of enzymes and inhibitors.

Urokinase plasminogen activator's major function is in tissue-related proteolysis, and is important in the processes that entail the dissolution of the extracellular matrix and invasion of the basement membranes. It is produced by cells and is present in extracellular fluid in the form of an inactive, single chain proenzyme (pro-uPA). Conversion of pro-uPA to active two-chain uPA by catalytic amounts of plasmin is a crucial regulatory step in plasminogen activation. This conversion provides active uPA and enables an autocatalytic acceleration of uPA formation, (Mayer, M., 1990, Biochemical and Biological Aspects of the Plasminogen Activation System, Clin. Biochem, 23:197-211) uPA is over expressed on the surface of cancer cells when compared with their normal noncancerous counterparts or normal physiological levels of this enzyme.

2.2. Plasminogen Activator Inhibitor Type 1 (PAI-1)

PAI-1 is considered one of the principal regulators of the plasminogen activator system. It is a single chain glycoprotein with a molecular weight of 50 kDa (Van Mourik J A et al., J Biol Chem (1984) 259:14914-14921) and is the most efficient inhibitor known of the single- and two-chain forms of tPA and of uPA (Lawrence D et al., Eur J Biochem (1989) 186:523-533). PAI-1 also inhibits plasmin and trypsin (Hekman C M et al., Biochemistry (1988) 27:2911-2918) and also inhibits thrombin and activated protein C, though with much lower efficiency.

PAI-1 has significant homology with members of the serine protease inhibitor (serpin) family. Serpins share structural features and are important regulators of physiological processes. Among many binding partners, PAI-1 protein also interacts with integrin at the integrin docking site. The PAI-1 forms 1:1 complexes between tPA and uPA inactivating them completely. Although PAI-1 is synthesized in an active form, it is rapidly converted to an inactive (latent) form.

PAI-1 is present in plasma at very low concentrations, ranging from 0 to 60 ng/ml (average of about 20 ng/ml or 0.5 nM) (Declerck P J et al., Blood (1988) 71:220-225) and a reported half-life of about 6-7 minutes (Vaughan D E et al., Circ Res (1990) 67:1281-1286). In a study comparing the clearance of two distinct forms of PAI-1 (active and latent), the active form was cleared biphasically (half-lives of 6 and 25 minutes), whereas latent PAI-1 was cleared with a half-life of only 1.7 minutes (Mayer E J et al., Blood (1990) 76:1514-1520).

Plasma PAI-1 is present as a complex with vitronectin (Vn) or S protein (Declerck P J et al., J Biol Chem (1988) 263:15454-15461). PAI-1 is also associated with Vn in the ECM in culture and may be involved in maintaining the integrity of the cell substratum in vivo (Mimuro J et al., Blood (1987) 70:721-728; Mimuro J et al., J Biol Chem (1989) 264:5058-5063).

Although uPA inhibitors have been implicated in induction of tumor cell growth, most known uPA inhibitors are unstable, weak or toxic in humans. Accordingly, there is a need for stable, effective and non-toxic or, at least, less toxic uPA inhibitors. Although PAI-1 lacks toxicity; it is rapidly inactivated, by conversion to the latent form, in vivo. Accordingly, active PAI-1 molecules with longer in vivo half-lives would be useful anti-cancer and for anti-angiogenesis agents.

2.2.1. PAI-1 Protein Structure and Function

PAI-1 cDNA encodes a protein of 402 amino acids that includes a typical secretion signal sequence (Ny et al., supra; Ginsburg et al., 1986, supra) (See FIGS. 1-4). Mature human PAI-1 isolated from cell culture is composed of two variants of 381 and 379 amino acids in approximately equal proportions. These two forms, likely arising from alternative cleavage of the secretion signal sequence, provide proteins with overlappimg amino-terminal sequences of Ser-Ala-Val-His-His and Val-His-His-Pro-Pro (Lawrence et al., 1989, supra). This latter sequence is generally referred to as mature PAI-1.

PAI-1 is a glycoprotein with three potential N-linked glycosylation sites containing between 15 and 20% carbohydrate (Van Mourik J A et al., supra). PAI-1 produced in E. coli, although nonglycosylated, is functionally very similar to native PAI-1. Recombinant PAI-1 can be isolated from E. coli in an inherently active form (see Section 2.2.2.), which contrasts with PAI-1 purified from mammalian cell culture (Lawrence et al., 1989, supra; Hekman et al, 1988, supra).

2.2.2. Active and Latent Conformation

PAI-1 exists in an active form as it is produced by cells and secreted into the culture medium and an inactive or latent form that accumulates in the culture medium over time (Hekman C M et al., J Biol Chem (1985) 260:11581-11587; Levin E G et al., Blood (1987) 70:1090-1098). The active form spontaneously converts to the latent form with a half-life of about 1 h at 37° C. (Lawrence et al., supra; Hekman et al., supra; Levin E G et al., 1987, supra). PAI-1 is a specific and fast acting inhibitor of both the tissue plasminogen activator (tPA) and urokinase plasminogen activator (uPA). Like other serpins, PAI-1 has a reactive center located on a highly strained exposed loop near the C-terminus of the molecule. The "reactive center" of PAI-1 contains the "bait" peptide bond between residues R(346) and M(347) (M-methionine, R-arginine), i.e., the P1-P1' residues. This bond mimics the R(560)-V(561) (V-valine) bond of plasminogen, which is the bond cleaved by the plasminogen activators during the activation of plasminogen to plasmin. On the basis of the mechanism of the action of other serpins, it has been postulated that PAI-1 binds specifically to the plasminogen activators like substrates (Seetharm R., et al., 1992, Biochemistry, 31:9877-9882).

The structure of active PAI-1 differs significantly from its inactive form. The latent form of PAI-1 has a greater number of residues from the strained reactive center loop inserted between the A3 strand and the A5 strand in the deducted structure of PAI-1, leading to a collapse of the strained loop and loss of inhibitory activity. Latent PAI-1 is inactive because part of its reactive center loop is inaccessible or does not have conformation to bind to its cognate proteases. The residues expected to interact with Ala 357 to Glu 362 all reside in the extended loop on the surface of the molecule. The helix D loop comprises amino acids approximately at positions 92-107 of the PAI-1 amino acid sequence (as depicted in FIG. 2A, or corresponding residues in other PAI-1 proteins as determined by, e.g., sequence analysis). The A3 strand comprises amino acids approximately at positions 341-353. The A4 strand comprises amino acids approximately at positions 353-374. The A5 strand comprises amino acid approximately at positions 180-197. In the latent form, the A4 strand of the β-sheet, which is the reactive loop, is buried in the PAI-1 molecule between the A3 strand and the A5 strand, and the reactive loop is not accessible for binding to uPA. However, in the active form, when the A4 strand slides out, the A3 strand and the A5 strand are not separated by any gap, but come close together and maintain the uniform β-sheet.

The latent form can be converted into the active form by treatment with denaturants, negatively charged phospholipids, guanidine hydrochloride, or vitronectin (Lambers et al., supra, Hekman et al., supra; Wun T-C et al, J Biol Chem (1989) 264:7862-7868). Latent PAI-1 infused into rabbits becomes reactivated in vivo by an unknown mechanism. The reversible interconversion between the active and latent structures, presumably due to a conformational change, is a unique feature of PAI-1 as compared to other serpins. The latent form appears to be more energetically favored.

Figure 6B:
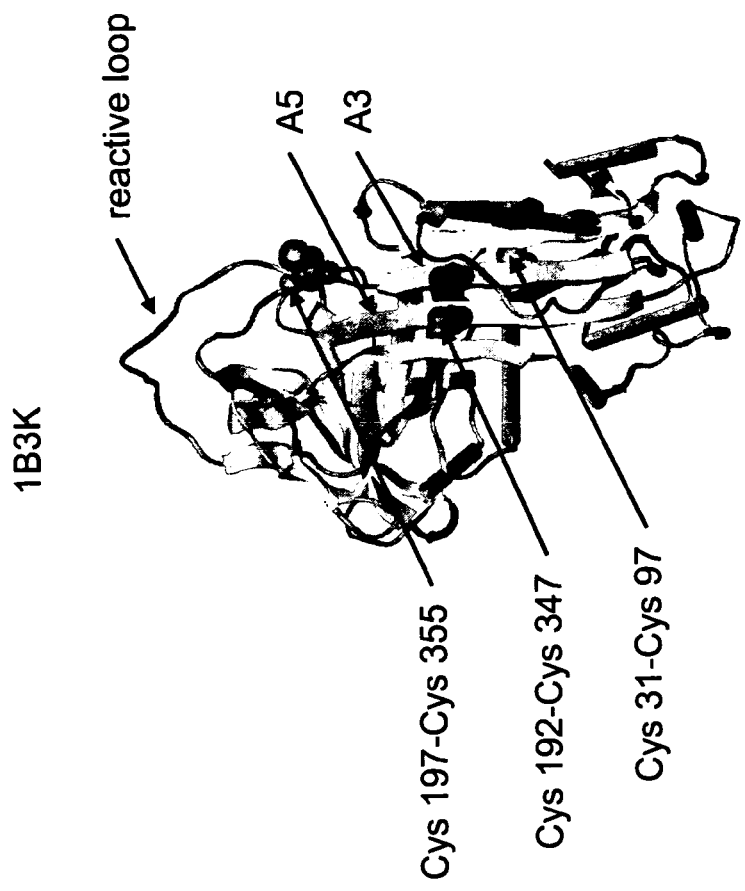

The three dimensional structure of the latent form of PAI 1 has been solved. In this structure the entire N terminal side of the reactive center loop is inserted as the central strand into β-sheet A (FIG. 6A) (Mottonen et al., supra) which explains the increased stability (Lawrence, D. A. et al., Biochemistry 33:3643 3648 (1994)) as well as the lack of inhibitory activity. It has been proposed that the reactive center in active PAI 1 is exposed as a surface loop, in contrast to its position in the latent structure (FIG. 6B.).

Active PAI-1 can be stored at −70° C. for months with minimal loss in its activity and negligible conversion to the latent form. However, it will be appreciated that PAI-1 loses about 50% of its activity after 2 hours at 37° C. due to conversion of PAI-1 to the latent form (significant conversion of PAI-1 to the latent form also occurs at 4° C.). This conversion represents a major challenge in the process to purify, conjugate and store large quantities of active PAI-1 or its conjugates. The latent form of PAI-1 can be reactivated by employing the denaturing agents (6 M guanidium chloride, 1% sodium dodecyl sulfate and others), or more conveniently through heat treatment. Under these conditions the PAI-1 undergoes complete unfolding and can be refolded to its active form after removing the denaturing agents, yielding near 100% of its original activity. Unfortunately, the PAI-1 spontaneously reverses to its latent form again, as quickly as described above. In general, although theoretically useful in the treatment of cancer and other conditions, uPA inhibitors are toxic or labile. PAI-1 is not toxic but the active form has a short half-life. Hence, there is a need to provide a modified PAI-1 in which the active form has a longer half-life.

3. SUMMARY OF THE INVENTION

The present invention is based upon the observation of the present inventors that a modified PAI-1 protein in which two or more amino acid residues that do not contain a sulfhydryl group have been replaced with amino acid residues that contain sulfhydryl groups such as, but not limited to, cysteine residues, that form one or more intramolecule disulfide bonds, has a much longer in vivo half-life of the active form of PAI-1 than a wild-type PAI-1 protein, in which there is no such disulfide bond or other introduced stabilizing modification (Chorostowska-Wynimiko et al., 2003, Molecular Cancer Therapeutics 2:19-28). These modified PAI-1 proteins are generated by amino acid substitutions of certain amino acid residues with cysteine residues to produce disulfide bridges linking the A3 strand and the A5 strand of the β-sheet of the PAI-1 protein (see FIG. 6). The mutations introduced into the PAI-1 protein do not significantly reduce the PAI-1 enzymatic activity (or does not reduce the enzymatic activity to an extent that is not compensated by the increase in in vivo half-life) but can increase the half-life of the active form of the modified PAI-1 when compared to wild-type PAI-1.

Inhibitors of urokinase plasminogen activator (uPA) strongly suppress angiogenesis and consequently limit cancer growth. The majority of known small-molecular inhibitors of uPA are toxic and nonspecific, while plasminogen activator inhibitor type 1 (PAI-1) is non-toxic and highly specific for uPA. Unfortunately, PAI-1 converts to a latent, inactive form with a half-life ($t_{1/2}$) of approximately 2 hrs. The present invention is aimed at providing modified PAI-1 proteins (and functionally active fragments, derivatives and analogs thereof) ("collectively, "modified PAI-1 molecules") with increased in vivo half-life of the active form of modified PAI-1 (as determined, for example, in Section 5.6), and preferably, with increased binding to uPA. By introducing amino acid residues that contain a sulfhydryl group into the PAI-1 polypeptide such that intramolecular disulfide bonds are formed, the $t_{1/2}$ of PAI-1 can be extended to therapeutically desired values.

Active PAI-1 has a reactive loop containing a P1-P1' site (Arginine 346 and Methionine 347 which form the "bait" i.e., mimics plasminogen) which can extend up to 18 Å from the body of the molecule. While in latent form, this loop is placed between the A3 strand and A5 strand, as described supra, of the corresponding β-sheet, rendering the P1-P1' site inaccessible to uPA. The present inventors have discovered that the in vivo half-life of PAI-1 protein may be extended by modification of the structure of PAI-1. In particular, by restraining the movement of the A3 strand and the A5 strand, as well as limiting the flexibility of the helix D region, as defined supra, it is possible to prevent insertion of the reactive loop between A3 strand and A5 strand. Such a modification extends the half-life of PAI-1 protein. Based on the known structure of active PAI-1, amino acid residues within the amino acid sequence of PAI-1 have been identified that can be substituted with cysteine residues to produce disulfide bridges linking the top and bottom parts of the A3 strand and the A5 strand as well as sites within the helix D region. Desired mutations may be introduced by any method known in the art, for example, by PCR using appropriate primers. Modification of the PAI-1 protein may be produced by site-directed mutagenesis to substitute the codon for an amino acid with the codon for cysteine in a nucleic acid sequence encoding PAI-1. In a preferred embodiment, two, four, or six amino acid substitutions may be introduced, thus promoting the formation of one, 2 or 3 disulfide bridges. In a specific embodiment, one or more disulfide bridges may be formed to bridge the top and bottom parts of the A3 strand and the A5 strand, within the helix D region.

The present invention relates to modified plasminogen activator inhibitor type-1 (PAI-1) polypeptides, comprising substitution of amino acid residues that do not contain a sulfhydryl group with amino acid residues that contain a sulfhydryl group, such as cysteine residues, such that one or more intramolecular disulfide bonds are formed, having a longer in vivo half-life of the active form of modified PAI-1 than a PAI-1 protein which has no cysteine residues or disulfide bonds (or other chemical cross-linking). In another embodiment, amino acid residues other than a methionine residue may be substituted with a methionine residue. The number of amino acid residues that may be substituted with disulfide containing residues may be 1, 2, 3, 4, 5, 6, 7, 8, 9, 10, or more than 10 and less than 20, more than 20 and less than 30. Preferably, the substitutions are made in pairs, i.e.,: 2, 4, 6, 8, or 10 substitutions with sulfhydryl containing residues are made. The invention also includes modified PAI-1 polypeptides having one or more additional amino acid substitutions that are not substitutions with a residue having a sulfhydryl group, particularly, where such a modified PAI-1 molecule retains one or more PAI-1 activities. In a preferred embodiment, the present invention provides modified PAI-1 molecules with mutations at amino acid positions located near or within the β-sheet so that disulfide bridges may stabilize or restrain the A3 and A5 strands of the β-sheet preventing the insertion of the active loop, i.e., the A4 strand, between the A3 and A5 strands of the β-sheet. Most preferably, the modified PAI-1 molecules have increased in vivo half-life of the active form of modified PAI-1, for example but not limited to, by virtue of disulfide bridges formed between the A3 strand and the A5 strand of the β-sheet. The disulfide bridges may be formed, most preferably, by introducing two, four, or six cysteine residues located near or within the β-sheet. The methods of making the foregoing by chemical synthesis or recombinant DNA technology are within the scope of the invention and are routine in the art.

In another preferred embodiment, the present invention provides modified PAI-1 proteins having at least two or more amino acid substitutions in the sequence from amino acid positions 10-40, 70-120, 150-220, 300-342, 343-350, or 351-402 of SEQ ID NO:2, more preferably in positions 31, 97, 192, 197, 347, 355 of SEQ ID NO:2 (or analogous residues in another PAI-1 molecule as determined, for example, by sequence alignment). In another embodiment, the present invention provides modified PAI-1 proteins having at least two or more amino acid substitutions in the sequence from amino acid positions 1-40, 41-120, 121-220, 221-290, 300-342, 343-350, or 351-402 of SEQ ID NO:2. In more preferred embodiments, one or more pairs of amino acid residues selected from the pairs Valine 31 and Alanine 97, or Leucine 192 and Valine 347, or Glutamine 197 and Glycine 355, are both replaced with cysteine residues. In a more preferred embodiment, Valine 31, Alanine 97, Leucine 192 and Valine 347 are replaced with cysteine residues. In more preferred embodiments, one or more disulfide bridges are formed between amino acid positions 31 and 97, 192 and 347, or 197 and 355. In preferred embodiments, the modifications result in holding the A3 strand and A5 strand of the β-sheet close together. In specific embodiments, the distance between the A3 strand and A5 strand of the β-sheet is less than 0.5 Å, more than 0.5 Å and not more than 2 Å, more than 2 Å and not more than 4 Å, more than 4 Å and not more than 10 Å, more than 10 Å and not more than 20 Å, or more than 20 Å and not more than 40 Å. In preferred embodiments, one or more disulfide bridges are formed at or near amino acid positions 10-40, 70-120, 150-220, 300-350, or 351-400. Most preferably, one or more disulfide bridges are formed at or near residues 180-370.

The present invention relates to modified PAI-1 proteins and functionally active fragments, derivatives and analogs thereof ("modified PAI-1 molecules"), preferably having one or more substitutions of amino acid residues (as described hereinbelow) that result in an increased in vivo half-life of the active form of the modified PAI-1 molecules. Preferably, the in vivo half-life of the active form of PAI-1 molecules is over 3 hours, 6 hours, 10 hours, 12 hours, 20 hours, 50 hours, 60 hours, 70 hours, 90 hours, 96 hours, 100 hours, 150 hours, 200 hours, 300 hours, 400 hours, 500 hours, 600 hours, 700 hours, 800 hours, or 900 hours. In specific embodiments, the in vivo half-life of the active form of PAI-1 molecules is greater than 6 hours, 11 hours, 12 hours, 61 hours, 73 hours, 96 hours, 165 hours, 8 days, 1 week, or 2 weeks. In a particular embodiment, the active form of PAI-1 molecule is locked in the active form over an extended period of time for over 2 weeks, 4 weeks, or 2 months.

The present invention relates to modified PAI-1 molecules having one or more substitutions, deletions or insertions of amino acid residues or other mutations (as described hereinbelow) to increase in vivo half-life of the active form of the PAI-1 molecules. In preferred embodiments, modified PAI-1 molecules of the invention are more active than wild-type PAI-1 protein in binding uPA and also have prolonged half-life of the active form of the modified PAI-1 molecules in circulation.

Also provided are nucleotide sequences encoding modified PAI-1 molecules and host-vector systems for expression of modified PAI-1 molecules. In a preferred embodiment, modified PAI-1 molecules may be expressed using a bacterial expression vector.

The present invention further provides pharmaceutical compositions containing the modified PAI-1 protein molecules of the invention. The modified PAI-1 molecules of the present invention also augment endogenous PAI-1 functions. The present invention further provides methods of therapeutic use of modified PAI-1 molecules in psoriasis, inflammatory disorders, diseases and disorders associated with excess angiogenesis, and primary and metastatic neoplastic diseases (e.g., cancer) and cardiovascular disease, particularly diseases and disorders associated with excess fibrinolysis. The modified PAI-1 molecules may be used for inhibition of angiogenesis or inhibition of other functions mediated or influenced by PAI-1 or uPA, including but not limited to cell proliferation, cell attachment, cell migration, granulation tissue development, and/or inflammation. The modified PAI-1 molecules of the present invention also inhibit tPA. Accordingly, the modified PAI-1 molecules of the present invention may be used to treat and prevent fibrinolysis or any diseases or disorders mediated by tPA. Modified PAI-1 molecules of the present invention may be used to reduce the proteolytic association with a cancer cell to decrease invasion and metastasis. In a preferred embodiment, modified PAI-1 molecules are used as anti-angiogenic agents to reduce tumor growth, and to inhibit primary and metastatic neoplastic diseases. In a preferred embodiment, modified PAI-1 molecules are used to block uPA proteolysis. The modified PAI-1 molecules of the invention may also be used to treat cardio-vascular diseases such as, but not limited to those that are related to hyperfibrinolysis, hemophilia, and vessel leakage syndrome.

4. DESCRIPTION OF THE FIGURES

FIGS. 1A-E. The nucleotide sequence (SEQ ID NO:1) encoding human PAI 1 plus 5' and 3' untranslated regions from a particular clone. Also shown is the amino acid sequence of full length human PAI 1 including the signal peptide (SEQ ID NO:2).

FIGS. 2A-2B. (A) The amino acid sequence of the PAI-1 protein (SEQ ID NO:2) including the signal peptide. (B) The amino acid sequence of the mature PAI-1 protein (SEQ ID NO:3).

FIG. 3. Percentage activity of wild-type PAI-1 vs. time elapsed as determined by amidolytic assay.

Figure 4:
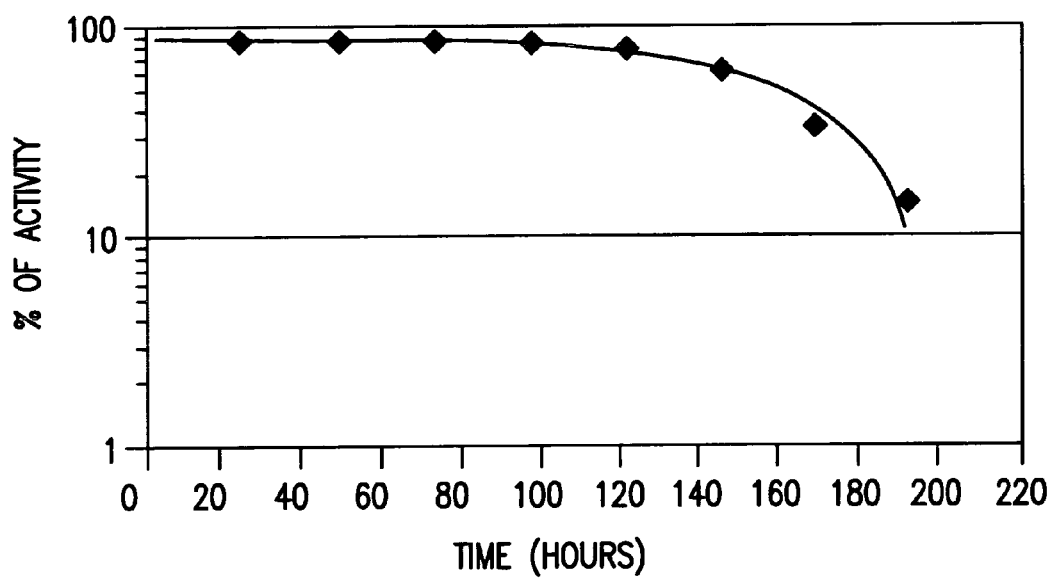

FIG. 4. Percentage activity of a modified PAI-1 protein with cysteine residue substitutions at amino acid positions 192 and 347 (β-sheet b) vs. time elapsed as determined by amidolytic assay.

Figure 5:
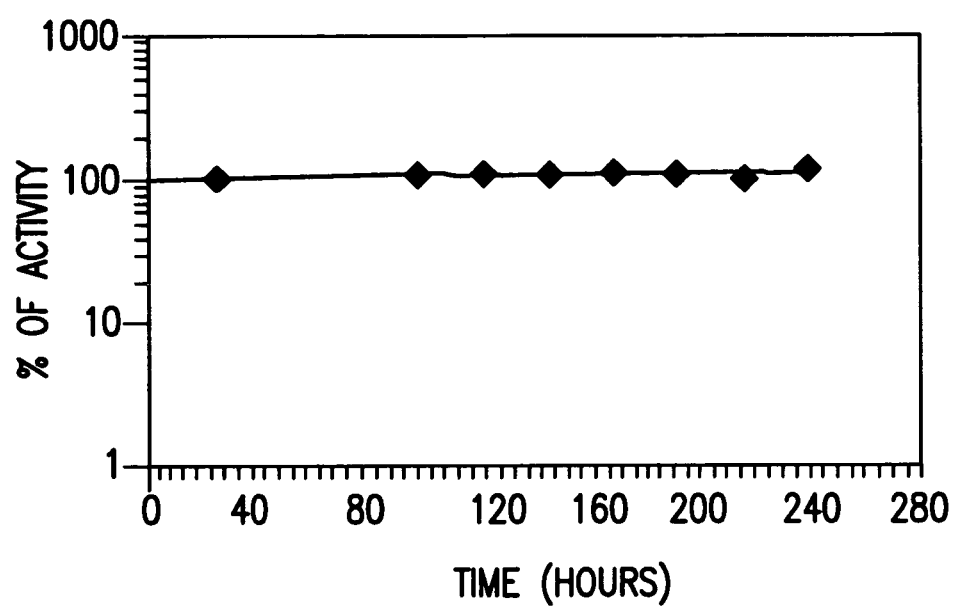

FIG. 5. Percentage activity of a modified PAI-1 protein with cysteine residue substitutions at amino acid positions 197 and 355 (β-sheet t) vs. time elapsed as determined by amidolytic assay.

Figure 6A:
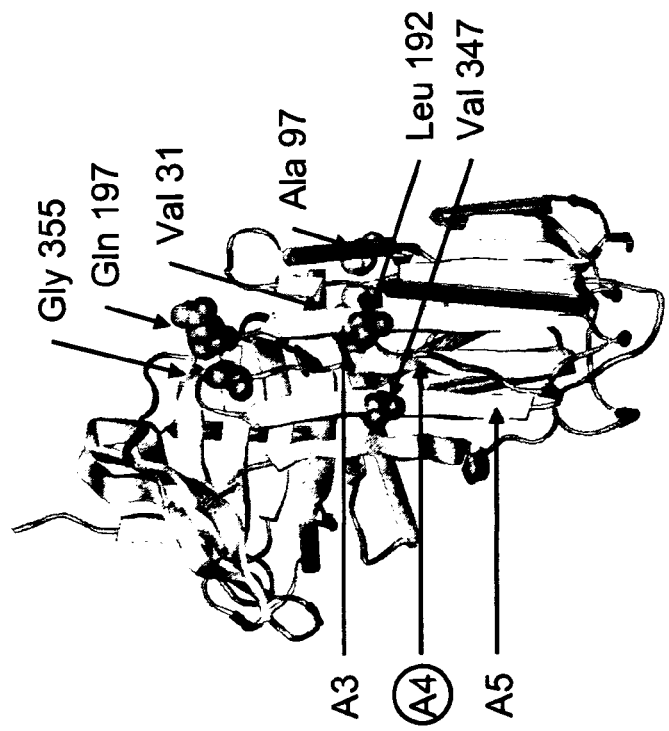

FIGS. 6A & 6B. (A) Ribbon model of latent form of PAI-1. (B) Ribbon model of active form of a modified PAI-1. On the left side amino acids that were mutated are shown as CPK model (balls), on the right, disulfide bridges are shown in CPK model. From the bottom: Cys 31-Cys 97 (helix D) bridge reduces flexibility of PAI-1 molecule by holding together N terminal to the nearest helix; Cys 192-Cys 347 (β sheet b) bridge tightly holds A3-A5 strands, most upper one: Cys 197-Cys 355 ((β sheet t) ends stiffening the reactive loop and preventing its backtracking into the β sheet. Models of active PAI-1 and latent form were acquired from X-ray analysis, PAI-1-VHLH was built using CHAIN program. Please note that all amino acids are numbered as in notation commonly accepted for thrombin, while in some publications and other public data base entries the amino acid numbering could be different.

Figure 7:
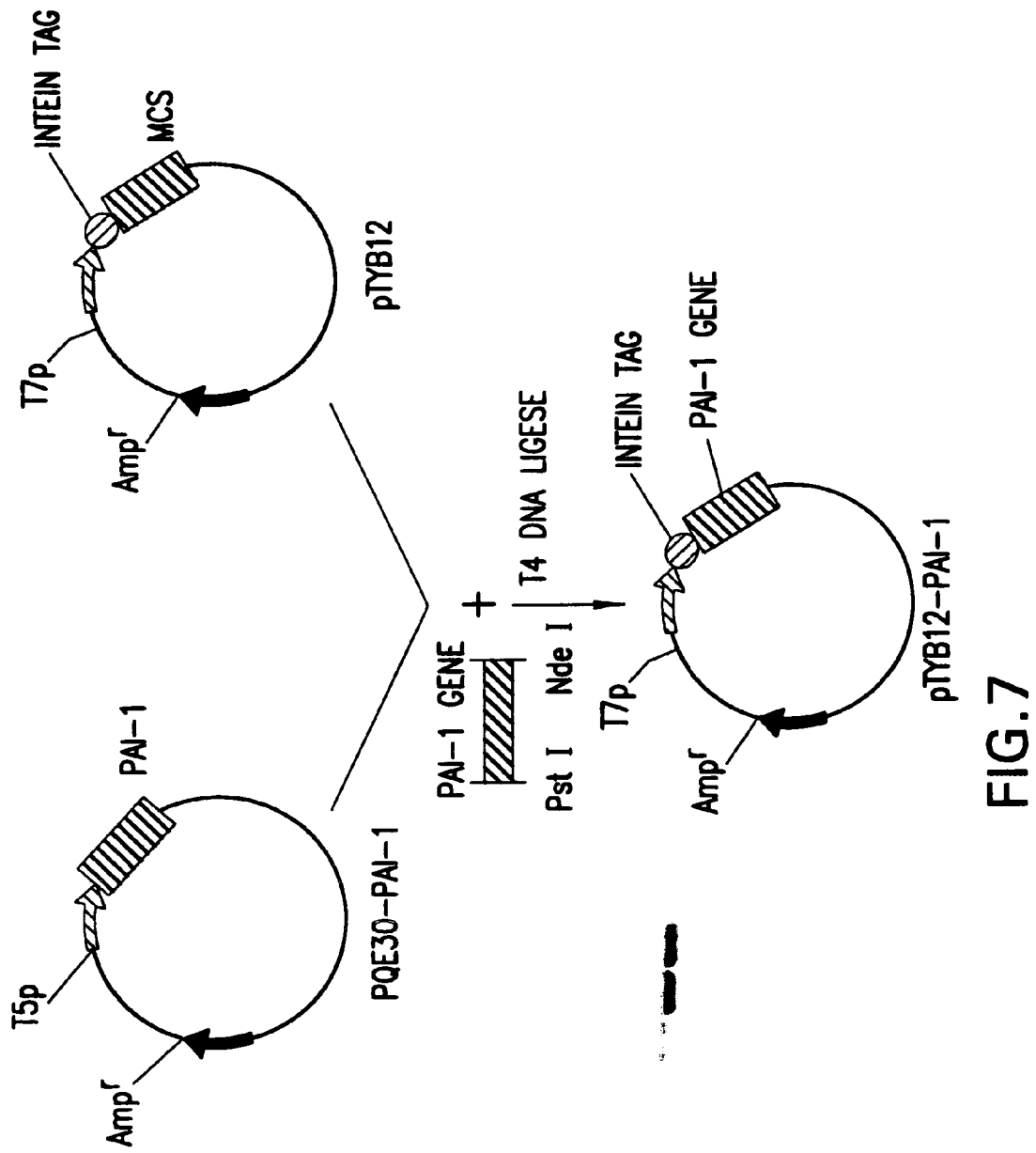

FIG. 7. Construction of plasmid pTYB12-PAI-1 from plasmid pQE30-PAI-1 and pTYB12 for the production of a modified PAI-1 protein.

Figure 8A:
Figure 8B:

FIGS. 8A & B. Measurement of anti-angiogenic activity of modified PAI-1 protein in a sprout formation assay. (A) Aggregate of human umbilical vein endothelial cells (HUVEC) were treated with benzamidine (31 µm). (B) Non-treated control. Dark areas in the center of FIG. 8A and upper left hand of FIG. 8B are aggregates of HUVEC cells. Elongated, thread like structures in FIG. 8B are sprouts. The assay was performed using B428 at a concentration of 40 nM and PAI-1 starting at a concentration of 1.0 µM.

Figure 9A:
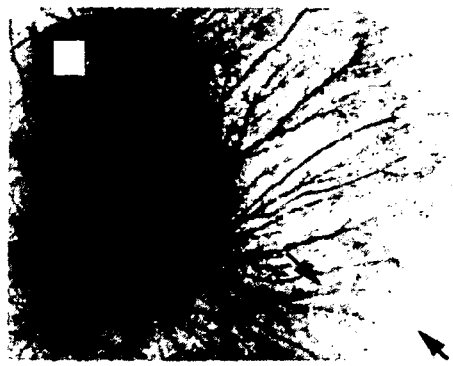
Figure 9B:

FIGS. 9A & 9B. Inhibition of angiogenesis by uPA inhibitor in chicken chorionic membranes in a chicken chorioallantoic membrane (CAM) assay. (A—control; B—30 µg of amiloride). Black arrows indicate approximate position of methylcellulose disk. The same assay was performed using other uPA inhibitors and with 40 µg of modified PAI-1 protein.

Figure 10:
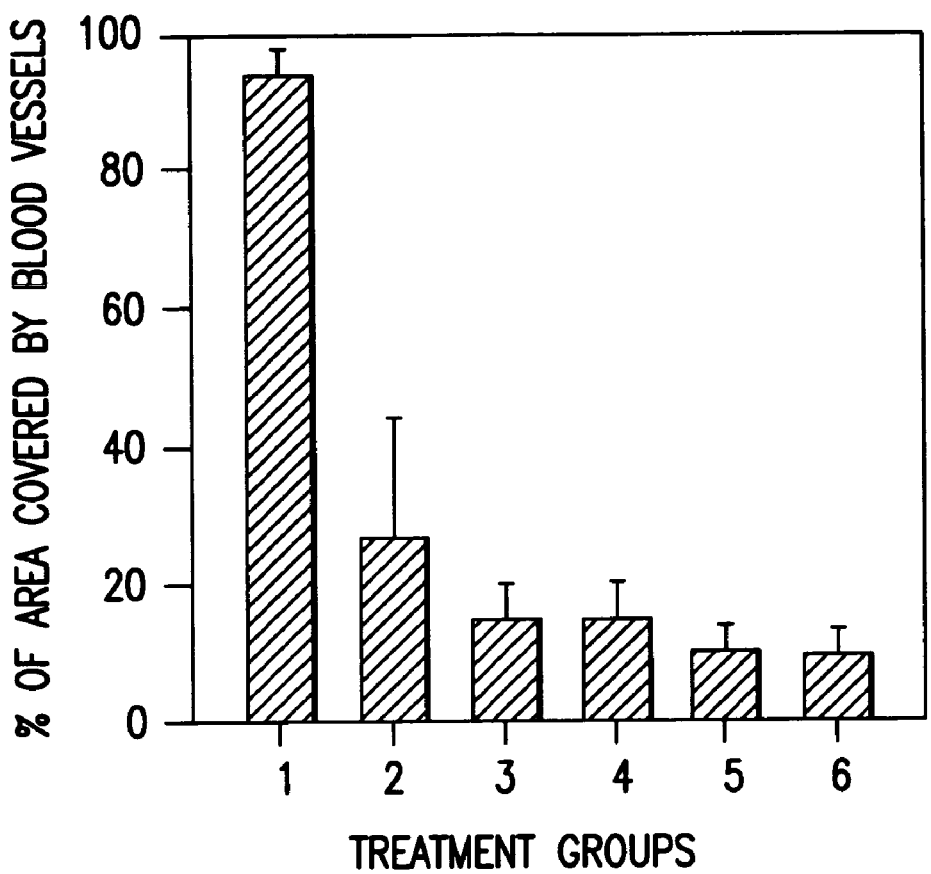

FIG. 10. Bar graph for measuring angiogenesis in chicken chorioallantoic membrane (CAM) assay. Percentage of area covered by blood vessels was quantified by computer analysis: 1 control, chick embryo treated with modified PAI-1 protein at various amounts: 2-20 µM, 3-40 µM, 4-60 µM, 5-80 µM, 6-100 µM.

Figure 11:
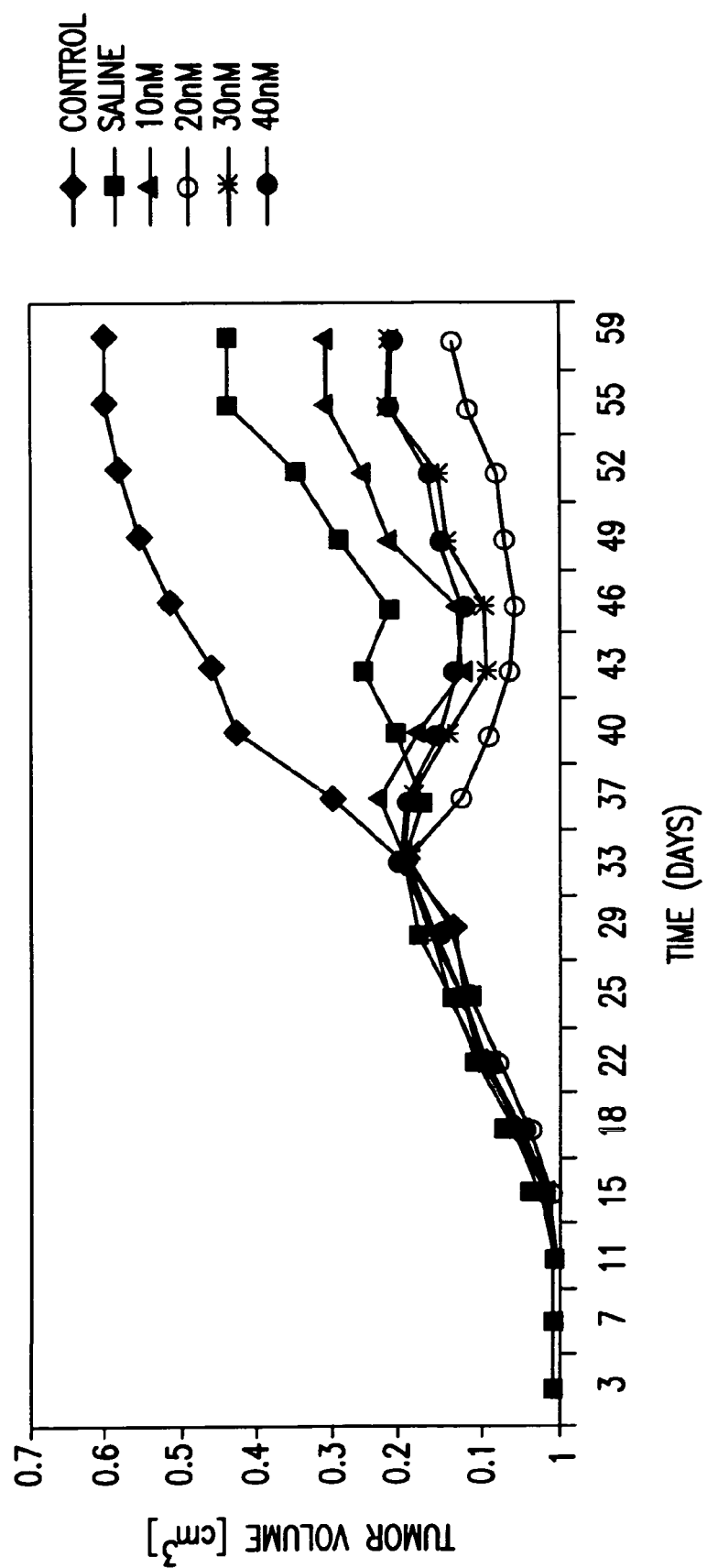

FIG. 11. Tumor volume of treated and non-treated SCID mice innoculated with LNCaP cells was measured over time. For the control, no treatment was given. The rest of the mice were given saline or various doses of modified PAI-1 protein; 10 nM, 20 nM, 30 nM, or 40 nM.

Figure 12:
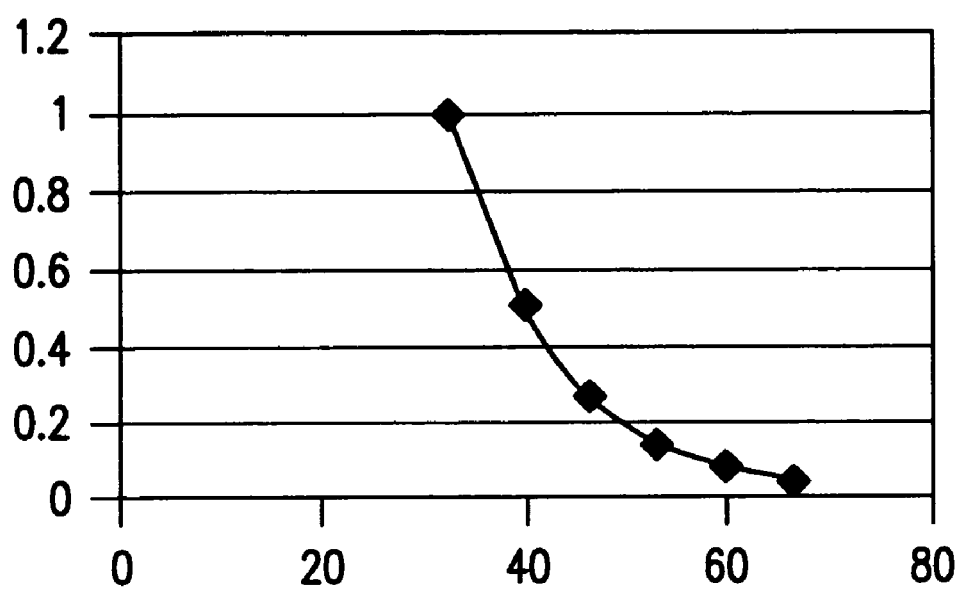

FIG. 12. Activity of modified PAI-1 protein is measured over time (days). Modified PAI-1 protein gradually converted from an active form to a latent form. After 60 days, only less than 6% of the original activity remains.

5. DETAILED DESCRIPTION OF THE INVENTION

The present invention relates to novel modified PAI-1 proteins and functionally active fragments, derivatives and analogs thereof ("modified PAI-1 molecules of the invention"), nucleic acid molecules encoding modified PAI-1 proteins molecules as well as therapeutic and prophylactic methods using modified PAI-1 molecules of the invention. The present inventors have designed and made modified PAI-1 molecules that have mutations (preferably amino acid substitutions) in or close to the β-sheet of PAI-1 which increase the bioactivity of PAI-1, in particular, to increase the half-life of the PAI-1 active form in circulation. The invention provides modified PAI-1 molecules in which two or more amino acid residues that do not contain a sulfhydryl group have been replaced with amino acid residues that contain sulfhydryl groups such as, but not limited to, cysteine residues, so that these sulfhydryl containing residues form one or more intrachain disulfide bonds, which modified PAI-1 molecules have a much longer half-life than a wild type PAI-1 protein.

In preferred embodiments, the amino acid residues to be substituted with sulfhydryl containing groups are amino acids having aliphatic side chains such as, but not limited to, glycine, alanine, valine, leucine, isoleucine. In other preferred embodiments, the amino acid residues to be substituted with sulfhydryl containing groups are amino acids having amide side chains such as, but not limited to, asparagine or glutamine. The disulfide bonds introduced into PAI-1 preferably hold the A3 strand and A5 strand of the β-sheet together so as to prevent the insertion of A4 strand between the A3 strand and A5 strand of the β-sheet. As discussed above, the helix D loop comprises amino acids at positions 92-107. The A3 strand comprises amino acids at positions 341-353. The A4 strand comprises amino acids at positions 353-374. The A5 strand comprises amino acid at positions 180-197. In particular preferred embodiment, the modified PAI-1 molecule has two or more amino acid substitutions with a sulfhydryl group in pairs at amino acids 31 and 97, 192 and 347, or 197 and 355 of the human PAI-1 (as depicted in FIG. 2A (SEQ ID NO:2), or analogous residues in other PAI-1 proteins as determined by sequence alignment). And most preferably, the modified PAI-1 molecule is modified to increase in vivo half-life of the active form of the modified PAI-1 molecule, for example but not limited to, forming disulfide bridges between the A3 strand and the A5 strand of the β-sheet. The disulfide bridges may be formed most preferably by introducing two, four, or six cysteines located near or within the β-sheet.

The methods of making the foregoing by chemical synthesis or recombinant DNA technology are within the scope of the invention and the skill in the art.

In another preferred embodiment, the present invention provides a modified PAI-1 molecule having at least one amino acid substitution at one of amino acid positions 10-40, 70-120, 150-220, 300-342, 343-350, or 351-400 of SEQ ID NO:2, more preferably at one of positions 31, 97, 192, 197, 347, or 355 of SEQ ID NO:2. In a preferred embodiment, the modified PAI-1 molecule comprises at least one amino acid substitution in the sequence from amino acid positions 29-32, 92-107, 180-197, 341-353, 353-374, 246-249, or 381-391. In a preferred embodiment, the present invention provides a modified PAI-1 molecule having two or more amino acid substitutions, most preferably, in pairs of amino acid substitutions. In particular, if an amino acid at positions 10-40 is substituted, another amino acid at positions 70-120 is substituted; if an amino acid at positions 150-220 is substituted, another amino acid at positions 300-350 is substituted. Most preferably, the present invention provides a modified PAI-1 molecule having two or more amino acid substitutions, most preferred in pairs of amino acids at amino acid positions 31 and 97, 192 and 347, or 197 and 355 of the human PAI-1. In more preferred embodiments, one or more pairs of amino acid residues selected from the pairs Valine 31 and Alanine 97, or Leucine 192 and Valine 347, or Glutamine 197 and Glycine 355 are both replaced with cysteine residues. In the most preferred embodiment, the modified PAI-1 molecule comprises one pair of amino acid residue substitution at Glutamine 197 and Glycine 355.

In preferred embodiments, mutations are introduced such that disulfide bonds are formed so that the A3 strand and A5 strand of the β-sheet are held close together. In specific embodiments, the distance between the A3 strand and A5 strand of the β-sheet are less than 0.5 Å, more than 0.5 Å and not more than 2 Å, more than 2 Å and not more than 4 Å, more than 4 Å and not more than 10 Å, more than 10 Å and not more than 20 Å, more than 20 Å and not more than 40 Å as determined by x-ray crystallography, NMR, or molecular modelling. In preferred embodiments, one or more disulfide bridges are formed at or near helix D (amino acid positions 31 and 97), β-sheet t (amino acid positions 197 and 355), or β-sheet b (amino acid positions 192 and 347). Most preferably, one or more disulfide bridges are formed at or near β-sheet b and β-sheet t. Most preferably, a disulfide bridge is formed at or near β-sheet t. In more preferred embodiments, one or more disulfide bridges are formed between amino acid positions 31 and 97, 192 and 347, or 197 and 355.

The present invention relates to modified PAI-1 molecules in which the active form of the modified PAI-1 molecules have increased in vivo half-life. Preferably, the in vivo half-life is over 3 hours, 6 hours, 10 hours, 20 hours, 50 hours, 60 hours, 70 hours, 90 hours, 100 hours, 150 hours, 200 hours, 10 days, 12 days, 16 days, 30 days, or 60 days. In a particular embodiment, the active form of PAI-1 molecule is locked in the active form over an extended period of time for over 2 weeks, 4 weeks, or 2 months.

In other embodiments, the modified PAI-1 molecules retain 100%, greater than 90%, 80%, 70%, 60%, 50%, 40%, 30%, 20%, or 10% of activity compared to a wild-type PAI-1 protein.

The present invention also relates to modified PAI-1 molecules having one or more deletions or insertions of amino acid residues (as described hereinbelow) in which the active form of the modified PAI-1 molecules have increased in vivo half-life. In preferred embodiment, the modified PAI-1 molecules are more active than the wild-type PAI-1, for example, but not limited to, binding to uPA or tPA, and active form of the modified PAI-1 molecules have prolonged half-lives in circulation. In certain embodiments, the modified PAI-1 molecules are 1.5, 2, 3, 10, or 20 times more active than the wild-type PAI-1.

Modified molecules, fusion proteins, and nucleic acid molecules encoding such molecules, and production of the foregoing molecules, e.g., by recombinant DNA methods, are also provided.

In particular aspects, the invention provides amino acid sequences of modified PAI-1 molecules, which are otherwise functionally active. "Functionally active" modified PAI-1 protein as used herein refers to that material displaying one or more known functional activities associated with the wild-type protein, e.g., binding to uPA or tPA; or inactivation or inhibition of uPA or tPA activity, internalization of uPA/PAR complex, antigenicity (binding to an anti-PAI-1 antibody), immunogenicity, or eliciting production of anti-PAI-1 antibodies, etc.

In specific embodiments, the invention provides fragments of modified PAI-1 consisting of at least 6 amino acids, 10 amino acids, 50 amino acids, 75 amino acids, 100 amino acids, 150 amino acids, 200 amino acids, 250 amino acids, 300 amino acids, or 349 amino acids. In various embodiments, the modified PAI-1 comprises or consists essentially of a mutated helix D, β-sheet b, β-sheet t or combinations thereof.

The present invention further provides nucleic acid molecules comprising nucleotide sequences that encode modified PAI-1 proteins, and methods of using the nucleic acid molecules, for example for recombinant production of the modified PAI-1 proteins of the invention or gene therapy. The mutations in the PAI-1 nucleic acid molecules are described in greater detail in Section 5.4 hereinbelow.

The present invention also relates to therapeutic and prophylactic methods and pharmaceutical compositions based on modified PAI-1 molecules. The invention provides for the use of modified PAI-1 molecules of the invention in the treatment of disorders and diseases associated with increased angiogenic activity and cell proliferation, e.g., psoriasis, rheumatoid arthritis, immune disorders, chronic inflammation, inflammatory bowel diseases, other inflammatory disorders, primary and metastatic neoplastic disease (e.g. cancer), in particular, metastatic disease, by administering modified PAI-1 molecules in which the active form has a longer half-life in circulation than the wild type PAI-1. The invention may also be used to treat cardio-vascular diseases such as, but not limited to those that are related to hyperfibrinolysis, hemophilia, and vessel leakage syndrome.

For clarity of disclosure, and not by way of limitation, the detailed description of the invention is divided into the subsections which follow.

5.1. Modified PAI-1 Molecules

The present inventors have made modified PAI-1 molecules which confer on these modified PAI-1 molecules new and useful properties, including, but not limited to, increased in vivo half-life of the active form of the modified PAI-1 molecules (as determined, e.g., by the method described in Section 5.6 infra; and increased ability to bind to a binding partner, including, but not limited to, uPA. The present invention provides a modified PAI-1 with mutations at amino acid positions located near or within the β-sheet so that disulfide bridges may be formed that hold the A3 strand and the A5 strand of the β-sheet closer together, thus preventing the insertion of the A4 strand between the A3 strand and the A5 strand of the β-sheet. The present invention provides a modified PAI-1 molecule in which two or more amino acid residues that do not contain a sulfhydryl group have been replaced with amino acid residues that contain sulfhydryl groups such as, but not limited to, cysteine residues, that form one or more intrachain disulfide bonds, which having a much longer in vivo half-life of the active form of the modified PAI-1 molecules than a PAI-1 protein, such as a wild-type PAI-1 protein, in which there is no such disulfide bond or other added stabilizing interaction not present in wild-type PAI-1. Modified PAI-1 proteins comprise amino acid sequence in which two or more amino acid residues other than a cysteine residue or methionine residue are substituted with a cysteine residue or methionine residue. The number of amino acid residues that may be substituted in a modified PAI-1 being 1, 2, 3, 4, 5, 6, 7, 8, 9, 10, or more than 10 and less than 20, more than 20, preferably, an even number of amino acid residues are substituted.

According to the invention, the modified PAI-1 molecules comprise substitutions, deletions or insertions, of two, four, six, or more amino acid residues with respect to the wild-type protein.

In one embodiment, the modified PAI-1 molecule has one or more substitutions of amino acid residues relative to the wild type PAI-1 protein, preferably, two or more amino acid substitutions in the amino acid residues selected from among residues at positions 10-40, 70-120, 150-220, or 300-400 of SEQ ID NO:2. More preferably in positions 31, 97, 192, 197, 347, 355 of SEQ ID NO:2 (or analogous residues in another PAI-1 molecule as determined, for example, by sequence alignment). In a preferred embodiment, the modified PAI-1 molecule comprises at least one amino acid substitution in the sequence from amino acid positions 29-32, 92-107, 180-197, 341-353, 353-374, 246-249, or 381-391.

In more preferred embodiments, one or more pairs of amino acid residues selected from the pairs Valine 31 and Alanine 97, or Leucine 192 and Valine 347, or Glutamine 197 and Glycine 355 are each replaced with cysteine residues. In more preferred embodiments, one or more disulfide bridges are formed at amino acid positions 31 and 97, 192 and 347, or 197 and 355.

In other embodiments, the modified PAI-1 molecule comprises other amino acid changes as well as long as the PAI-1 activity and/or half life of the active form of the modified PAI-1 molecule are increased.

In one particular non-limiting set of embodiments, other covalent bonds may be formed that hold the A3 strand and the A5 strand of the β-sheet closer together, thus preventing the insertion of the A4 strand between the A3 strand and the A5 strand of the β-sheet. Methods of chemical cross-linking include, for example, using an amine-sulfhydryl cross-linker such as N-(α-maleimidoacetoxy)-succinimide ester ("AMAS") or N-(κ-maleimidoundecanoyloxy)-sulfosuccinimide ester ("KMUS") (Pierce Chemical Co.). Such methods would generally involve reductive methylation of one protein to block N-termini, cross-linking of blocked peptide at pH 6.5-7.5 using sulfo-KMUS or AMAS, and reacting the succinimide group of the modified protein with the other protein at pH 8-9. Other methods which are well known in the art may also be able to used to form intramolecular covalent bonds useful in the present invention.

5.2. Nucleic Acid Molecules Encoding Modified PAI-1

The present invention also relates to nucleic acid molecules comprising sequences encoding modified human PAI-1 molecules of the invention, wherein the sequences contain at least two or more base insertions, deletions or substitutions, or combinations thereof that result in two or more amino acid additions, deletions and substitutions in the expression product of the nucleotide sequences relative to the wild type PAI-1. Base mutations that do not alter the reading frame of the coding region are preferred.

Due to the degeneracy of nucleotide coding sequences, any other DNA sequences that encode the same amino acid sequence for a modified PAI-1 molecule may be used in the practice of the present invention. These include but are not limited to nucleotide sequences comprising all or portions of the coding region of the PAI-1 gene which are altered by the substitution of different codons that encode the same amino acid residue within the sequence, thus producing a silent change.

In one embodiment, the present invention provides nucleic acid molecules comprising sequences encoding modified PAI-1 molecules, wherein the modified PAI-1 molecules comprises two or more amino acid substitutions, preferably located at or near the β-sheet (as described in Section 5.1). In a specific embodiment, the invention provides nucleic acids encoding modified PAI-1 molecules having amino acid substitutions at positions 31 and 97 of the amino acid sequence of the PAI-1 molecule as depicted in FIG. 2A (SEQ ID NO:2), preferably, substitution with methionine, more preferably substitution with cysteine. The present invention further provides nucleic acid molecules comprising sequences encoding modified PAI-1 molecules comprising two or more amino acid substitutions, preferably located at or near the β-sheet. In preferred embodiments, one or more disulfide bridges are formed at or near helix D, β-sheet b, or β-sheet t, or combination thereof. Most preferably, one or more disulfide bridges are formed at or near β-sheet b and β-sheet t.

The modified PAI-1 nucleic acid molecules of the invention can be made by recombinant methods known in the art, and expressing the protein by methods commonly known in the art. Alternatively, such modified PAI-1 molecules may be made by protein synthetic techniques, e.g., using of a peptide synthesizer.

5.3. Therapeutic and Prophylactic Methods for Cancer/Disorders Associated with Increase Angiogenisis The invention provides for methods of treatment, prophylaxis, management or amelioration of one or more symptoms associated with the disease, disorder using modified PAI-1 molecules of the invention. These diseases and disorders include, but are not limited to, diseases or disorders related to angiogenesis or other functions mediated or influenced by PAI-1, uPA, or tPA, including but not limited to cell proliferation, cell attachment, cell migration, granulation tissue development, primary and metastatic neoplastic diseases (e.g. cancer), and/or inflammation, cardiovascular disease, stroke, ischemia, or atherosclerosis.

The present invention encompasses methods for treating or preventing diseases and disorders wherein the treatment or prevention would be improved by administration of the modified PAI-1 molecules of the present invention.

In one embodiment, "treatment" or "treating" refers to an amelioration of disease or disorder, or at least one discernible symptom thereof. In another embodiment, "treatment" or "treating" refers to an amelioration of at least one measurable physical parameter associated with disease or disorder not necessarily discernible by the subject. In yet another embodiment, "treatment" or "treating" refers to inhibiting the progression of a disease or disorder either physically, e.g., stabilization of a discernible symptom, physiologically, e.g., stabilization of a physical parameter, or both. In yet another embodiment, "treatment" or "treating" refers to delaying the onset of a disease or disorder.

In certain embodiments, the methods and compositions of the present invention are useful as a preventative measure against disease or disorder. As used herein, "prevention" or "preventing" refers to a reduction of the risk of acquiring a given disease or disorder.

In certain embodiments, the invention provides methods for treating or preventing diseases or disorders comprising administration of a modified PAI-1 molecule in combination with other treatments.

The most notable property of cancer is its ability to invade and metastasize. Proteolytic activity driven by urokinase plasminogen activator (uPA) or other proteolytic enzymes, such as metalloproteinases, cysteine and serine proteinases are able to degrade the extracellular matrix. Highly metastatic cells synthesize various classes of degenerative enzymes and release them at higher concentrations or activities than their normal counterparts. (Jankun J., et al., 1991, Cancer Res. 51:1221-1226; Jankun J., et al., 1993, J. Cellular Biochem. 53:135-144). In a number of different tumor models, as well as in tissues derived from human malignancies, a direct correlation has been found between levels of urokinase plasminogen activator activity and/or concentration and the metastatic potential of cancer cells (Jankun et al., 1991, supra.).

It has been proposed that reduction of the cancer cell's proteolytic activity will decrease invasion and metastasis. uPA inhibitors have an important, but limited application in therapy, since in many cases, metastatic micro foci have already formed at the time of diagnosis. Proteolysis is responsible for degradation of proteins, for invasion and metastasis, but not for the proliferative properties of the cancer cells. The inhibitors of uPA, such as modified PAI-1 of the present invention may be interacting with the elements of the extracellular matrix, which also express uPA. The present invention further demonstrated that uPA inhibitors inhibit angiogenesis and thereby reduce tumor size.

PAI-1 is a member of the super-class of Serine Protease Inhibitors (SERPIN) which, in this case, has a demonstrated important role is cancer or tumor control, via blocking of the SERPIN active site of its protein protease target molecules, such as tissue-type plasminogen activator, or more importantly, urokinase plasminogen activator. PAI-1 targets urokinase on the urokinase receptor, thereby causing internalization, and thus, killing the tumor cell, i.e., without the PAI-1 conjugated to a cytotoxic. PAI-1 also carries docking sites for the integrin α₃β₂, which participates in tumor cell mobility. Additionally, PAI-1 has vitronectin docking sites, which stabilize the PAI-1/urokinase/urokinase receptor complex on the tumor cell surface. α₃β₂ also binds vitronectin.

Modified PAI-1 molecules of the present invention with extended half-life of the active form is a potent anti-angiogenic agent. By blocking uPA proteolysis, the modified PAI-1 molecules of the present invention can reduce tumor growth and inhibit metastasis. Furthermore, modified PAI-1 molecules of the present invention can prevent interaction of certain adhesion molecules so that cell migration can be diminished or halted, with a number of important consequences for those diseases and conditions associated with undesirable cell migration, which leads to proliferation and pathogenesis. Such migration is important in tumor invasion and metastasis, which can be suppressed by the present compositions and methods. Thus, modified PAI-1 can inhibit angiogenesis, an effect which can be harnessed to inhibit both local and metastatic tumor growth. Thus, the methods of the present invention may be used for the treatment of diseases and disorders related to angiogenesis or inhibition of other functions mediated or influenced by PAI-1, uPA, tPA, including but not limited to cell proliferation, primary and metastatic neoplastic diseases, e.g. cancer, cell attachment, cell migration, granulation tissue development, and/or inflammation. Accordingly, the invention provides methods of treating, preventing, managing or ameliorating cancer, particularly metastatic cancer by administration of modified PAI-1 molecules of the invention.

Cancers and related disorders that can be treated or prevented by methods and compositions of the present invention include but are not limited to the following: Leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but not limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

Accordingly, the methods and compositions of the invention are also useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal orignin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosafcoma, rhabdomyoscarama, and osteosarcoma; and other tumors, including melanoma, xenoderma pegmentosum, keratoactanthoma, seminoma, thyroid follicular cancer and teratocarcinoma. It is also contemplated that cancers caused by aberrations in apoptosis would also be treated by the methods and compositions of the invention. Such cancers may include but not be limited to follicular lymphomas, carcinomas with p53 mutations, hormone dependent tumors of the breast, prostate and ovary, and pre-cancerous lesions such as familial adenomatous polyposis, and myelodysplastic syndromes. In specific embodiments, malignancy or dysproliferative changes (such as metaplasias and dysplasias), or hyperproliferative disorders, are treated or prevented in the ovary, bladder, breast, colon, lung, skin, pancreas, or uterus. In other specific embodiments, sarcoma, melanoma, or leukemia is treated or prevented.

In preferred embodiments, the methods and compositions of the invention are used for the treatment and/or prevention of breast, colon, ovarian, lung, and prostate cancers and melanoma and are provided below by example rather than by limitation.

In specific embodiments, malignancy or dysproliferative changes (such as metaplasias and dysplasias), or hyperproliferative disorders, are treated or prevented in the ovary, bladder, breast, colon, lung, skin, pancreas, or uterus. In other specific embodiments, sarcoma or melanoma is treated or prevented.

The modified PAI-1 molecules of the invention can be administered to treat premalignant conditions and to prevent progression to a neoplastic or malignant state. Such prophylactic or therapeutic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 197, *Basic Pathology* 2d Ed., W.B. Saunders Co., Philadelphia, pp. 8-79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of the modified PAI-1 molecules. As mentioned supra, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84-90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia) is indicative of the desirability of prophylactic intervention.

In other embodiments, a patient which exhibits one or more of the following predisposing factors for malignancy is treated by administration of an effective amount of the modified PAI-1 molecules of the invention: a chromosomal location associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 197, *Basic Pathology,* 2d Ed., W.B. Saunders Co., Philadelphia, pp. 112-113) etc.).

In another specific embodiment, the modified PAI-1 molecules of the invention is administered to a human patient to prevent progression to ovary, breast, colon, lung, pancreatic, skin, prostate, gastrointestinal, B lymphocyte, T lymphocyte or uterine cancer, melanoma or sarcoma.

The invention encompasses methods for treating or preventing a cancer or metastasis in a subject comprising in any order the steps of administering to the subject a modified PAI-1 molecule. In certain embodiments, the compositions and methods of the invention can be used to prevent, inhibit or reduce the growth or metastasis of cancerous cells. In a specific embodiment, the administration of a modified PAI-1 molecule inhibits or reduces the growth or metastasis of cancerous cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth or metastasis in absence of the administration of said modified PAI-1 molecule.

The invention encompasses methods of disease treatment or prevention that provide better therapeutic profiles than current single agent therapies or even current combination therapies. Encompassed by the invention are combination therapies that have additive potency or an additive therapeutic effect while reducing or avoiding unwanted or adverse effects. The invention also encompasses synergistic combinations where the therapeutic efficacy is greater than additive, while unwanted or adverse effects are reduced or avoided.

Other cancer treatment that may be used in combination of the administration of the modified PAI-1 molecules of the present invention include the use of one or more molecules, or compounds for the treatment of cancer (i.e., cancer therapeutics), which molecules, compounds or treatments include, but are not limited to, chemoagents, immunotherapeutics, cancer vaccines, anti-angiogenic agents, cytokines, hormone therapies, gene therapies, biological therapies, and radiotherapies. While maintaining or enhancing efficacy of treatment, preferably the methods of the present invention increase patient compliance, improve therapy and/or reduce unwanted or adverse effects.

In a specific embodiment, the methods of the invention encompass the administration of one or more angiogenesis inhibitors such as but not limited to: Angiostatin (plasminogen fragment); antiangiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; Combrestatin; A-4; Endostatin (collagen XVIII fragment); Fibronectin fragment; Gro-beta; Halofaginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAb IMC-1C11; Neovastat; NM-3; Panzem; PI-88; Placental ribonuclease inhibitor; Plasminogen activator inhibitor; Platelet factor-4 (PF4); Prinomastat; Prolactin 16 kD fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-b); Vasculostatin; Vasostatin (calreticulin fragment); ZD6126; ZD 6474; farnesyl transferase inhibitors (FTI); and bisphosphonates.

Additional examples of anti-cancer agents that can be used in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetiner; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramnustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene;

dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilnofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. These two agents are particularly useful when used in methods employing thalidomide and a topoisomerase inhibitor.

In one embodiment, one or more chemoagents are administered together or conjugated together with the modified PAI-1 molecules of the invention ("Therapeutics" of the present invention") to treat a cancer patient. A chemoagent (or "anti-cancer agent" or "anti-tumor agent" or "cancer therapeutic") refers to any molecule or compound that assists in the treatment of tumors or cancer. Examples of chemoagents include, but are not limited to, cytosine arabinoside, taxoids (e.g., paclitaxel, docetaxel), anti-tubulin agents (e.g., paclitaxel, docetaxel, epothilone B, or its analogues), macrolides (e.g., rhizoxin) cisplatin, carboplatin, adriamycin, tenoposide, mitozantron, discodermolide, eleutherobine, 2 chiorodeoxyadenosine, alkylating agents (e.g., cyclophosphamide, mechlorethamine, thioepa, chlorambucil, meiphalan, carmustine (BSNU), lomustine (CCNU), cyclothosphamide, busulfan, dibromomannitol, streptozotocin, mitomycin C, and cis-dichlorodiamine platinum (II) (DDP) cisplatin, thiotepa), antibiotics (e.g., dactinomycin (formerly actinomycin), bleomycin, mithramycin, anthramycin), antimetabolites (e.g., methotrexate, 6-mercaptopurine, 6-thioguanine, cytarabine, flavopiridol, 5-fluorouracil, fludarabine, gemcitabine, dacarbazine, temozolamide), asparaginase, Bacillus Calmette Guerin, diphtheria toxin, hexamethylmelamine, hydroxyurea, LYSODREN® (mitotane), nucleoside analogues, plant alkaloids (e.g., Taxol, paclitaxel, camptothecin, topotecan, CAMPTOSAR®, CPT-11 (irinotecan), vincristine, vinca alkyloids such as vinbiastine), podophyllotoxin (including derivatives such as epipodophyllotoxin, VP-16 (etoposide), VM-26 (teniposide)), cytochalasin B, colchine, gramicidin D, ethidium bromide, emetine, mitomycin, procarbazine, mechlorethamine, anthracyclines (e.g., daunorubicin (formerly daunomycin), doxorubicin, doxorubicin liposomal), dihydroxyanthracindione, mitoxantrone, mithramycin, actinomycin D, procaine, tetracaine, lidocaine, propranolol, puromycin, anti-mitotic agents, abrin, ricin A, pseudomonas exotoxin, nerve growth factor, platelet derived growth factor, tissue plasminogen activator, aldesleukin, allutamine, anastrozle, bicalutamide, biaomycin, busulfan, capecitabine, carboplatin, chlorabusil, cladribine, cylarabine, daclinomycin, estramusine, floxuride, gamcitabine, goserine, idarubicin, itosfamide, lauprolide acetate, levamisole, Lomusline, mechlorethamine, magestrol, acetate, mercaptopurino, mesna, mitolanc, pegaspergase, pentoslatin, picamycin, riuxlmab, campath-1, straplozocm, thioguanine, tretinoin, vinorelbine, or any fragments, family members, or derivatives thereof, including pharmaceutically acceptable salts thereof.

In other embodiments, the method for the treatment of cancers further comprises administration of pharmaceutical compositions comprising 5-fluorouracil, cisplatin, docetaxel, doxorubicin, HERCEPTIN® (trastuzumab), gemcitabine (Seidman, 2001, Oncology 15:11 14), IL-2, paclitaxel, and/or VP-16 (etoposide). In another embodiment, pharmaceutical compositions comprises modified PAI-1 molecules of the present invention conjugated with the above agents.

In another embodiment, the treatment of the present invention further includes the administration of one or more immunotherapeutic agents, such as antibodies and immunomodulators, which include, but are not limited to, HERCEPTIN® (trastuzumab), RITUXAN® (rituximab), OVAREX™ (oregovomab), PANOREX® (edrecolomab), BEC2, IMC-C225, VITAXIN™, CAMPATH® 1H (alemtuzumab), Smart M195, LYMPHOCIDE™ (epratuzumab), Smart I D10, and ONCOLYM™ (1-131 LYM-1), rituximab, gemtuzumab, or trastuzumab.

In another embodiment, the treatment of the present invention further includes administering one or more anti-angiogenic agents, which include, but are not limited to, angiostatin, thalidomide, kringle 5, endostatin, other Serpins, antithrombin, 29 kDa N-terminal and 40 kDa C-terminal proteolytic fragments of fibronectin, 16 kDa proteolytic fragment of prolactin, 7.8 kDa proteolytic fragment of platelet factor-4, a 13-amino acid peptide corresponding to a fragment of platelet factor-4 (Maione et al., 1990, *Cancer Res*, 51:2077), a 14-amino acid peptide corresponding to a fragment of collagen I (Tolma et al., 1993, *J. Cell Biol*. 122:497), a 19 amino acid peptide corresponding to a fragment of Thrombospondin I (Tolsma et al., 1993, *J. Cell Biol*. 122: 497), a 20-amino acid peptide corresponding to a fragment of SPARC (Sage et al., 1995, *J. Cell. Biochem*. 57:1329-), or any fragments, family members, or derivatives thereof, including pharmaceutically acceptable salts thereof.

Other peptides that inhibit angiogenesis and correspond to fragments of laminin, fibronectin, procollagen, and EGF have also been described (see the review by Cao, 1998, *Prog. Mol. Subcell. Biol.* 20:161). Monoclonal antibodies and cyclic pentapeptides, which block certain integrins that bind RGD proteins (i.e., possess the peptide motif Arg-Gly-Asp), for example, endostatin, have been demonstrated to have anti-vascularization activities (Brooks et al., 1994, *Science* 264: 569; Hammes et al., 1996, *Nature Medicine* 2:529). Moreover, inhibition of the urokinase plasminogen activator receptor by receptor antagonists inhibits angiogenesis, tumor growth and metastasis (Min et al., 1996, *Cancer Res*. 56:2428-33; Crowley et al., 1993, *Proc Natl Acad. Sci. USA* 90:5021). Use of such anti-angiogenic agents is also contemplated by the present invention.

In another embodiment, the treatment method further comprise the use of radiation.

In another embodiment, the treatment method further comprises the administration of one or more cytokines, which includes, but is not limited to, lymphokines, tumor necrosis factors, tumor necrosis factor-like cytokines, lymphotoxin-a, lymphotoxin-b, interferon-a, interferon-b, macrophage inflammatory proteins, granulocyte monocyte colony stimulating factor, interleukins (including, but not limited to, interleukin-1, interleukin-2, interleukin-6, interleukin-12, interleukin-15, interleukin-18), OX40, CD27, CD30, CD40 or CD137 ligands, Fas-Fas ligand, 4-1BBL, endothelial monocyte activating protein or any fragments, family members, or derivatives thereof, including pharmaceutically acceptable salts thereof.

In yet another embodiment, the treatment method further comprises hormonal treatment. Hormonal therapeutic treatments comprise hormonal agonists, hormonal antagonists (e.g., flutamide, tamoxifen, leuprolide acetate (LUPRON™), LH-RH antagonists), inhibitors of hormone biosynthesis and processing, steroids (e.g., dexamethasone, retinoids, betamethasone, cortisol, cortisone, prednisone, dehydrotestosterone, glucocorticoids, mineralocorticoids, estrogen, testosterone, progestins), antigestagens (e.g., mifepristone, onapristone), and antiandrogens (e.g., cyproterone acetate).

The methods of the present invention may be used for the inhibition of angiogenesis or inhibition of other functions mediated or influenced by PAI-1, uPA, or tPA, including but not limited to cell proliferation, primary and metastatic neoplastic diseases, cell attachment, cell migration, granulation tissue development, and/or autoimmune disorders or inflammatory diseases.

Examples of autoimmune disorders include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Ménière's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, and chronic inflammation resulting from chronic viral or bacteria infections. Some autoimmune disorders are associated with an inflammatory condition. Thus, there is overlap between what is considered an autoimmune disorder and an inflammatory disorder. Therefore, some autoimmune disorders may also be characterized as inflammatory disorders.

The present invention provides methods of preventing, treating, managing or ameliorating an autoimmune or inflammatory disorder or one or more symptoms thereof, said methods comprising administering to a subject in need of a modified PAI-1 molecules and one or more immunomodulatory agents. Preferably, the immunomodulatory agents are not administered to a subject with an autoimmune or inflammatory disorder whose mean absolute lymphocyte count is less than 500 cells/mm$^3$, less than 550 cells/mm$^3$, less than 600 cells/mm$^3$, less than 650 cells/mm$^3$, less than 700 cells/mm$^3$, less than 750 cells/mm$^3$, less than 800 cells/mm$^3$, less than 850 cells/mm$^3$ or less than 900 cells/mm$^3$. Thus, in a preferred embodiment, prior to or subsequent to the administration of one or more dosages of one or more immunomodulatory agents to a subject with an autoimmune or inflammatory disorder, the absolute lymphocyte count of said subject is determined by techniques well-known to one of skill in the art, including, e.g., flow cytometry or trypan blue counts.

Anti-inflammatories or immunomodulators may be used to prevent, manage, or ameliorate diseases, disorders, or infections related to inflammation.

Examples of immunomodulatory agents include, but are not limited to, methothrexate, leflunomide, cyclophosphamide, cyclosporine A, and macrolide antibiotics (e.g., FK506 (tacrolimus)), methylprednisolone (MP), corticosteroids, steriods, mycophenolate mofetil, rapamycin (sirolimus), mizoribine, deoxyspergualin, brequinar, malononitriloamindes (e.g., leflunamide), T cell receptor modulators, and cytokine receptor modulators. Examples of T cell receptor modulators include, but are not limited to, anti-T cell receptor antibodies (e.g., anti-CD4 monoclonal antibodies, anti-CD3 monoclonal antibodies, anti-CD8 monoclonal antibodies, anti-CD40 ligand monoclonal antibodies, anti-CD2 monoclonal antibodies) and CTLA4-immunoglobulin. Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, TNF-β, interferon (IFN)-α, IFN-β, IFN-γ, and GM-CSF), anti-cytokine receptor antibodies (e.g., anti-IL-2 receptor antibodies, anti-IL-4 receptor antibodies, anti-IL-6 receptor antibodies, anti-IL-10 receptor antibodies, and anti-IL-12 receptor antibodies), anti-cytokine antibodies (e.g., anti-IFN receptor antibodies, anti-TNF-α antibodies, anti-IL-1β antibodies, anti-IL-6 antibodies, and anti-IL-12 antibodies).

In a specific embodiment, the present invention provides a method for preventing, treating, managing or ameliorating an autoimmune or inflammatory disorder or one or more symptoms thereof, said method comprising administering to a subject in need thereof a prophylactically or therapeutically effective amount of modified PAI-1 molecules and a prophylactically or therapeutically effective amount of one or more immunomodulatory agents.

Anti-inflammatory agents have exhibited success in treatment of inflammatory and autoimmune disorders and are now a common and a standard treatment for such disorders. Any anti-inflammatory agent well-known to one of skill in the art can be used in the compositions and methods of the invention. Non-limiting examples of anti-inflammatory agents include non-steroidal anti-inflammatory drugs (NSAIDs), steroidal anti-inflammatory drugs, beta-agonists, anticholingeric agents, and methyl xanthines. Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketorolac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™. Such NSAIDs function by inhibiting a cyclooxgenase enzyme (e.g., COX-1 and/or COX-2). Examples of steroidal anti-inflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes.

Endogenous PAI-1 protein reduces natural fibrinolysis (blood vessel fibrin deposition and "clot busting"). At high levels, PAI-1 protein has a role in inhibiting fibrinolysis or in reversing hyperfibrinolysis. Accordingly, the modified PAI-1 molecules of the present invention are useful for the treatment, prophylaxis, management and amelioration of cardio-vascular diseases.

The modified PAI-1 molecules of the invention may also be used to treat cardio-vascular diseases such as, but not limited to those that are related to hyperfibrinolysis, hemophilia, and vessel leakage syndrome. In an embodiment, the modified PAI-1 molecules of the present invention may be used for acute clotting situations, i.e., tPA or uPA thrombolytic therapy overdose.

Gene therapy refers to treatment or prevention of a disease performed by the administration of a nucleic acid to a subject who has a disease. For example, the disease or disorder may be a cancer. In one embodiment of the invention, the therapeutic nucleic acid encodes a sequence that produces intracellularly (without a leader sequence) or intercellularly (with a leader sequence), a modified PAI-1 molecule and functionally active fragments, derivatives and analogs thereof.

For general reviews of the methods of gene therapy, see Goldspiel et al., 1993, *Clinical Pharmacy* 12:488-505; Wu and Wu, 1991, *Biotherapy* 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217). Methods commonly known in the art of recombinant DNA technology which can be used are described in Ausubel et al. (eds.), 1993, *Current Protocols in Molecular Biology*, John Wiley & Sons, NY; Kriegler, 1990, *Gene Transfer and Expression, A Laboratory Manual*, Stockton Press, NY; and in Chapters 12 and 13, Dracopoli et al. (eds), 1994, *Current Protocols in Human Genetics*, John Wiley & Sons, NY).

In one aspect, the therapeutic nucleic acid comprises an expression vector that expresses the modified PAI-1 protein and functionally active fragments, derivatives and analogs thereof.

Delivery of the nucleic acid into a patient may be either direct, in which case the patient is directly exposed to the nucleic acid or nucleic acid-carrying vector or a delivery complex, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the modified PAI-1 protein and functionally active fragments, derivatives and analogs thereof This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in biopolymers (e.g., poly-β-1->4-N-acetylglucosamine polysaccharide; see U.S. Pat. No. 5,635,493), encapsulation in liposomes, microparticles, or microcapsules, or by administering it in linkage to a peptide which is known to enter the nucleus, by administering it in linkage to a ligand which is known to enter the nucleus, by administering it in linkage to a ligand subject to receptor-mediated endocytosis (see e.g., Wu and Wu, 1987, *J. Biol. Chem.* 262:4429-4432), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Young). Alternatively, the nucleic acid can be introduced intracellularly and incorporated within host cell DNA for expression, by homologous recombination (Koller and Smithies, 1989, *Proc. Natl. Acad. Sci. USA* 86:8932-8935; Zijlstra et al., 1989, *Nature* 342:435-438).

Adenoviruses are other viral vectors that can be used in gene therapy. Adenoviruses are especially attractive vehicles for delivering genes to respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, *Current Opinion in Genetics and Development* 3:499-503 present a review of adenovirus-based gene therapy. Bout et al., 1994, *Human Gene Therapy* 5:3-10 demonstrated the use of adenovirus vectors to transfer genes to the respiratory epithelia of rhesus monkeys. Other instances of the use of adenoviruses in gene therapy can be found in Rosenfeld et al., 1991, *Science* 252:431-434; Rosenfeld et al., 1992, *Cell* 68:143-155; and Mastrangeli et al., 1993, *J. Clin. Invest.* 91:225-234. Adeno-associated virus (AAV) has also been proposed for use in gene therapy (Walsh et al., 1993, *Proc. Soc. Exp. Biol. Med.* 204:289-300).

The form and amount of therapeutic nucleic acid envisioned for use depends on the type of disease and the severity of its desired effect, patient state, etc., and can be determined by one skilled in the art.

5.4. Preparation of Modified PAI-1 Molecules

The production and use of the modified PAI-1 proteins molecules of the invention are within the scope of the present invention. Described herein are methods for making the foregoing.

5.4.1. PAI-1 Gene Cloning

The nucleotide sequences of the cDNA and the gene encoding the human PAI-1 are published and provided herein as SEQ ID NO:1 (FIG. 1).

Coding regions for the PAI-1 protein can be obtained by standard procedures known in the art from cloned DNA (e.g., a DNA "library"), by chemical synthesis, by cDNA cloning, or by the cloning of genomic DNA, or fragments thereof, purified from the desired cell (see, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) Polymerase chain reaction (PCR) can be used to amplify sequences encoding the PAI-1 gene in a genomic or cDNA library. Synthetic oligonucleotides may be utilized as primers designed, for example, based upon the PAI-1 sequence provided in FIG. 1 (SEQ ID NO:1) to amplify by PCR sequences from a source (RNA or DNA), preferably a cDNA library. The DNA being amplified can include cDNA or genomic DNA from any human. After successful isolation or amplification of a segment of a protein, that segment may be molecularly cloned and sequenced, and utilized as a probe to isolate a complete cDNA or genomic clone. This, in turn, will permit the characterization the gene's nucleotide sequence, and the production of its protein product for functional analysis and/or therapeutic or diagnostic use, as described infra.

Alternatives to isolating the coding regions for the PAI-1 protein include, but are not limited to, chemically synthesizing the gene sequence itself from the published sequence. Other methods are possible and within the scope of the invention. The above-methods are not meant to limit the following general description of methods by which modified PAI-1 protein may be obtained.

The modified PAI-1 molecules may be derived from other PAI-1 homologs. These PAI-1 homologs may be obtained by screening genomic libraries from other animals. A PAI-1 analog preferably exhibits at least about 80% overall similarity at the amino acid level to the amino acid sequence depicted in FIG. 2, more preferably exhibits at least about 85-90% overall similarity to the amino acid sequence in FIG. 2 and most preferably exhibits at least about 95% overall similarity to the amino acid sequence in FIG. 2. Such nucleic acid molecule that hybridizes to another nucleic acid consisting of the complement of the DNA sequences that encode the amino acid sequence shown in FIG. 2 under moderately or low stringent conditions, e.g., hybridization to filter-bound DNA in 6×SSC at 45° C., and washing in 2×SSC at 50° C. (Ausubel F. M. et al., eds., 1989, Current Protocols in Molecular Biology, Vol. I, Green Publishing Associates, Inc., and John Wiley & sons, Inc., New York, at page 2.10.3).

The modified PAI-1 molecules may also be derived from other naturally occurring variants of PAI-1, and degenerate variants thereof. A PAI-1 analog preferably exhibits at least about 80% overall similarity at the nucleotide level to the nucleic acid sequence depicted in FIG. 1, more preferably exhibits at least about 85-90% overall similarity to the nucleic acid sequence in FIG. 1 and most preferably exhibits at least about 95% overall similarity to the nucleic acid sequence in FIG. 1. Such nucleic acid molecule that hybridizes to another nucleic acid consisting of the complement of the DNA sequences that encode the amino acid sequence shown in FIG. 2 under highly stringent conditions, e.g., hybridization to filter-bound DNA in 0.5 M $NaHPO_4$, 7% sodium dodecyl sulfate (SDS), 1 mM EDTA at 65° C., and washing in 0.1× SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at page 2.10.3). The degree of similarity can be determined by analyzing sequence data using a computer algorithm, such as those used by the BLAST computer program.

The identified and isolated PAI-1 gene can be inserted into an appropriate cloning vector for amplification of the gene sequence. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as pBR322 or pUC plasmid derivatives or the Bluescript vector (Stratagene). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and modified gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionation, can be done before insertion into the cloning vector.

In specific embodiments, transformation of host cells with recombinant DNA molecules that comprise the modified PAI-1 gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA. Copies of the gene are used in mutagenesis experiments to study the functional activities, and in vivo half-life of the active form of the modified PAI-1 and functionally active fragments, derivatives and analogs thereof.

5.4.2. Methods of Making Modified PAI-1 Molecules by Amino Acid Substitution with Cysteine The mutations present in the modified PAI-1 molecules of the invention can be produced by various methods known in the art. The manipulations which result in their production can occur at the gene or protein level. For example, the cloned coding region of the protein can be modified by any of numerous strategies known in the art (Sambrook et al., 1990, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of a modified PAI-1 molecule, care should be taken to ensure that the modified gene remains within the same translational reading frame, uninterrupted by translational stop signals, in the gene region where the PAI-1 molecule is encoded.

Additionally, the nucleic acid sequence encoding the PAI-1 molecule can be mutated in vitro or in vivo to create variations in coding regions (e.g., amino acid substitutions), and/or to create and/or destroy translation, initiation, and/or termination sequences, and/or form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson, C., et al., 1978, J. Biol. Chem 253:6551), PCR-based overlap extension (Ho et al., 1989, Gene 77:51-59), PCR-based megaprimer mutagenesis (Sarkar et al., 1990, Biotechniques, 8:404-407), etc. Mutations can be confirmed by double stranded dideoxy DNA sequencing.

In preferred embodiments, mutagenesis is used to substitute the codon for a particular amino acid residue with a codon for another amino acid residue, preferably an amino acid residue with a sulfhydryl group.

Two or more amino acid residues within a PAI-1 protein can be substituted by another amino acid residue, most preferably an amino acid residue that can form a disulfide bridge. The amino acid to be introduced within the sequence may be selected from members of the same or different class to which the amino acid being substituted belongs. The nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. In a most preferred embodiment, the substitutions result in a modified PAI-1 molecule that has an increased half-life of the active form.

In certain embodiments, a nucleic acid molecule encodes a modified PAI-1 protein in which the nucleic acid molecule comprises at least one or more nucleic acid substitutions from the triplet codon of the nucleic acid at positions 65-67, 364-366, 649-651, 664-666, 1114-1116, or 1138-1140 of SEQ ID NO:1 (or analogous residues in another PAI-1 molecule as determined, for example, by sequence alignment) to a triplet codon that recites TGT or TGC. The nucleic acid molecule thus encodes a modified PAI-1 protein in which there is one or more cysteine substitutions at one or more amino acid at: Valine 31, Alanine 97, Leucine 192 or Valine 347.

Manipulations of the modified PAI-1 protein sequence may also be made at the protein level. Included within the scope of the invention are modified PAI-1 protein molecules which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin, etc. In a most preferred embodiment, the modification results in a modified PAI-1 protein in which the active form has an increased in vivo half-life.

In certain embodiments, a modified PAI-1 proteins comprises at least two or more amino acid substitutions in the sequence from amino acid positions 10-40, 70-120, 150-220, 300-342, 343-350, or 351-400 of SEQ ID NO:2, more preferably in positions 31, 97, 192, 197, 347, 355 of SEQ ID NO:2 (or analogous residues in another PAI-1 molecule as determined, for example, by sequence alignment). In more preferred embodiments, one or more pairs of amino acid residues selected from the pairs Valine 31 and Alanine 97, or Leucine 192 and Valine 347, or Glutamine 197 and Glycine 355, are both replaced with cysteine residues. In a more preferred embodiment, Valine 31, Alanine 97, Leucine 192 and Valine 347 are replaced with cysteine residues.

In addition, modified PAI-1 proteins can be chemically synthesized. For example, a peptide corresponding to a portion of a modified PAI-1 protein which comprises the desired mutation can be synthesized by use of a peptide synthesizer. Furthermore, if desired, nonclassical amino acids or chemical amino acid analogs can be introduced as a substitution or addition into the modified PAI-1 protein sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In specific embodiments, the modified PAI-1 protein comprises a fusion protein that is produced by recombinant expression of a nucleic acid encoding a modified PAI-1 protein joined in-frame to the coding sequence for another protein, such as but not limited to toxins, such as ricin or diphtheria toxin. Such a fusion protein can be made by ligating the appropriate nucleic acid sequences encoding the desired amino acid sequences to each other by methods known in the art, in the proper coding frame, and expressing the fusion protein by methods commonly known in the art. Alternatively, such a fusion protein may be made by protein synthetic techniques, e.g., by use of a peptide synthesizer. Chimeric genes comprising portions of modified PAI-1 protein fused to any heterologous protein-encoding sequences may be constructed.

In other embodiments, the modified PAI-1 molecules are conjugated to a diagnostic or detectable agent. Such molecules can be useful for monitoring or prognosing the development or progression of a cancer as part of a clinical testing procedure, such as determining the efficacy of a particular therapy. Such diagnosis and detection can accomplished by coupling the modified PAI-1 molecules to detectable substances including, but not limited to various enzymes, such as but not limited to horseradish peroxidase, alkaline phosphatase, beta-galactosidase, or acetylcholinesterase; prosthetic groups, such as but not limited to streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In, $^{111}$In,), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, and noradioactive paramagnetic metal ions are radiolabelled or conjugated to specific radioisotopes.

The present invention further encompasses uses of modified PAI-1 molecules conjugated to a therapeutic agent.

A molecule may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Examples include paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Further, the modified PAI-1 molecules may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, J. Iminunol., 6:1567-1574), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

Moreover, the modified PAI-1 molecules may be conjugated to therapeutic moieties such as a radioactive metal ion, such as alph-emiters such as $^{213}$Bi or macrocyclic chelators useful for conjugating radiometal ions, including but not limited to, $^{131}$In, $^{131}$Lu, $^{131}$Y, $^{131}$Ho, $^{131}$Sm, to polypeptides. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., Clin Cancer Res. 4(10):2483-90 (1998); Peterson et al. Bioconjug. Chem. 10(4):553-7 (1999); and Zimmerman et al., Nucl. Med. Biol. 26(8): 943-50 (1999) each incorporated by reference in their entireties.

In specific embodiments, the modified PAI-1 molecule is conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Further, the modified PAI-1 molecules may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, J. Iminunol., 6:1567-1574), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")), a chemotherapeutic agent or other type of toxin, e.g., a ricin toxin, or a radionuclide, or any other agent effective to kill cancer or tumor cells or to arrest cancer cell growth. The modified PAI-1 molecules may be conjugated to an antibiotic, antifungal or anti-viral agent.

The term "derivative" as used herein also refers to a modified PAI-1 molecule which has been modified, i.e., by the covalent attachment of any type of molecule to the modified PAI-1 molecule. For example, but not by way of limitation, the modified PAI-1 molecules may be modified, e.g., by glycosylation, acetylation, pegylation, phosphorylation, amidation, derivatization by known protecting/blocking groups, proteolytic cleavage, linkage to a cellular ligand or other protein, etc. A derivative PAI-1 molecule may be produced by chemical modifications using techniques known to those of skill in the art, including, but not limited to specific chemical cleavage, acetylation, formylation, metabolic synthesis of tunicamycin, etc. Further, a derivative PAI-1 molecule may contain one or more non-classical amino acids. A PAI-1 derivative possesses a similar or identical function as the PAI-1 protein from which it was derived.

The nucleotide sequence coding for a modified PAI-1 protein, or a functionally active analog or fragment or other derivative thereof (see Section 5.2.1), can be inserted into an appropriate expression vector, i.e., a vector which contains the necessary elements for the transcription and translation of the inserted protein-coding sequence. The necessary transcriptional and translational signals can also be supplied by the human PAI-1 protein cDNA or gene, and/or genomic sequences flanking the two gene. A variety of host-vector systems may be utilized to express the protein-coding sequence. These include but are not limited to mammalian cell systems (e.g., COS, CHO, BHK, 293, NS0, and 3T3 cells) infected with virus (e.g., vaccinia virus, adenovirus, etc.), mammalian cells such as Chinese hamster ovary cells (CHO) in conjunction with a vector such as the major intermediate early gene promoter element from human cytomegalovirus (or promoters derived from the genome of mammalian cells (e.g., metallothionein promoter) or from mammalian viruses (e.g., the adenovirus late promoter, the vaccinia virus 7.5K promoter) are effective expression systems; insect cell systems infected with recombinant virus expression vectors (e.g., baculovirus); plant cell systems infected with recombinant virus expression vectors (e.g., cauliflower mosaic virus, CaMV; tobacco mosaic virus, TMV) or transformed with recombinant plasmid expression vectors (e.g., Ti plasmid); microorganisms such as bacteria (e.g., *E. coli* and *B. subtilis*) transformed with recombinant bacteriophage DNA, plasmid DNA or cosmid DNA expression vectors; yeast (e.g., *Saccharomyces Pichia*) containing recombinant yeast expression vectors. The expression elements of vectors vary in their strengths and specificities. Depending on the host-vector system utilized, any one of a number of suitable transcription and translation elements may be used. In specific embodiments, a modified human PAI-1 protein coding region, or a sequence encoding a mutated and functionally active portion of the respective modified PAI-1 protein is expressed.

Any of the methods previously described for the insertion of DNA fragments into a vector may be used to construct expression vectors containing a modified PAI-1 gene consisting of appropriate transcriptional/translational control signals and the protein coding sequences. These methods may include in vitro recombinant DNA and synthetic techniques and in vivo recombinants (genetic recombination). Expression of nucleotide sequence encoding a modified PAI-1 protein may be regulated by a second nucleotide sequence so that the modified PAI-1 protein is expressed in a host transformed with the recombinant DNA molecule. For example, expression of a modified PAI-1 protein molecule may be controlled by any promoter/enhancer element known in the art. Promoters which may be used to include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42).

In a preferred embodiment, the expression vector is pTYB 12-PAI-1.

In a specific embodiment, a vector is used that comprises one or more promoters operably linked to the coding region of a modified PAI-1 protein, an origin of replication, and, optionally, a selectable marker (e.g., an antibiotic resistance gene).

A host cell strain may be chosen which modulates the expression of the inserted sequences, or modifies and processes the gene product in the specific fashion desired. Expression from certain promoters can be elevated in the presence of certain inducers; thus, expression of the genetically engineered modified PAI-1 proteins may be controlled. Furthermore, different host cells have characteristics and specific mechanisms for the translational and post-translational processing and modification (e.g., glycosylation, phosphorylation of proteins). Appropriate cell lines or host systems can be chosen to ensure the desired modification and processing of the foreign protein expressed. Expression in mammalian cells can be used to ensure "native" glycosylation of a heterologous protein. Furthermore, different vector/host expression systems may effect processing reactions to different extent.

Once a recombinant host cell expresses the modified PAI-1 protein gene sequence, the gene product can be purified and analyzed. Methods of purification and analysis is well known in the art. Analysis of the modified PAI-1 protein may be achieved by assays based on the physical or functional properties of the product, including radioactive labeling of the product followed by analysis by gel electrophoresis, immunoassay, etc. In particular, in vivo half-life of the active form of the modified PAI-1 molecule is measured.

5.5. Generation of Antibodies to Modified PAI-1 Proteins and Analogs Thereof According to the invention, modified PAI-1 protein molecules may be used as an immunogen to generate antibodies which immunospecifically bind such an immunogen. Such antibodies include but are not limited to polyclonal, monoclonal, chimeric, single chain, Fab fragments, and an Fab expression library. In a specific embodiment, antibodies to a modified PAI-1 protein are produced. In another embodiment, antibodies to a fragment of a modified PAI-1 protein are produced. In a preferred embodiment, the antibodies against the modified PAI-1 do not bind to wild type PAI-1.

Various procedures known in the art may be used for the production of polyclonal antibodies to modified PAI-1 proteins and functionally active fragments, derivatives and analogs thereof. For the production of antibody, various host animals can be immunized by injection with the PAI-1 proteins and derivatives thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

For preparation of monoclonal antibodies directed toward modified PAI-1 protein molecules, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in *Monoclonal Antibodies and Cancer Therapy*, Alan R. Liss, pp. 77-96). In fact, according to the invention, techniques developed for the production of "chimeric antibodies" (Morrison et al., 1984, Proc. Natl. Acad. Sci. U.S.A. 81:6851-6855; Neuberger et al., 1984, Nature 312:604-608; Takeda et al., 1985, Nature 314:452-454) by splicing the genes from a mouse antibody molecule specific for the epitope together with genes from a human antibody molecule of appropriate biological activity can be used; such antibodies are within the scope of this invention.

According to the invention, techniques described for the production of single chain antibodies (U.S. Pat. No. 4,946,778) can be adapted to produce specific single chain antibodies against PAI-1 proteins or fragments or derivatives thereof. An additional embodiment of the invention utilizes the techniques described for the construction of Fab expression libraries (Huse et al., 1989, Science 246:1275-1281) to allow rapid and easy identification of monoclonal Fab fragments with the desired specificity.

Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, the Fab fragments which can be generated by treating the antibody molecule with papain and a reducing agent, and Fv fragments.

In the production of antibodies, screening for the desired antibody can be accomplished by techniques known in the art, e.g. ELISA (enzyme-linked immunosorbent assay). For example, to select antibodies which recognize a specific domain of a modified PAI-1 protein, one may assay generated hybridomas for a product which binds to a fragment of a modified PAI-1 protein containing such domain. Specific domains include, but are not limited to, helix D, β-sheet b, and β-sheet t. For selection of an antibody that specifically binds a modified PAI-1 protein but which does not specifically bind wild-type PAI-1, one can select on the basis of positive binding to the modified PAI-1 protein and a lack of binding to the wild-type protein. Antibodies specific to a domain of a modified PAI-1 protein are also provided.

The foregoing antibodies can be used in methods known in the art relating to the localization and activity of the modified PAI-1 proteins of the invention, e.g., for imaging these proteins, measuring levels thereof in appropriate physiological samples, in diagnostic methods, etc.

5.6. Structure Prediction and Functional Analysis of Modified PAI-1 Proteins The invention provides a modified PAI-1 molecule which has an extended in vivo half-life for the active form of the molecule. This is achieved by restraining the movement of the A3 strand and the A5 strand, as well as limiting the flexibility of the helix D region so as to prevent insertion of the reactive loop between the A3 strand and the A5 strand. Such conformation may be stabilized by bringing the A3 strand and the A5 strand close together. One way of bringing the A3 strand and the A5 strand is to create disulfide bonds between the A3 strand and the A5 strand by substituting amino acids without a sulfhydryl group at specific positions with an amino acid with a sulfhydryl group. Thus, it would be valuable if the structure of a modified PAI-1 molecule may be predicted based on the amino acid sequence. Structure prediction, analysis of crystallographic data, sequence alignment, as well as homology modeling, can be accomplished using computer software programs available in the art, such as BLAST, CHARMm release 21.2 for the Convex, and QUANTA v.3.3, (Molecular Simulations, Inc., York, United Kingdom).

Once a modified PAI-1 molecule is identified, it may be isolated and purified by standard methods including chromatography (e.g., ion exchange, affinity, and sizing column chromatography), centrifugation, differential solubility, or by any other standard technique for the purification of proteins. The in vitro activities and in vivo biological functions of the foregoing may be evaluated using any suitable assay (including immunoassays as described infra).

Alternatively, once a modified PAM-1 protein produced by a recombinant host cell is identified, the amino acid sequence of the PAI-1 protein(s) can be determined by standard techniques for protein sequencing, e.g., with an automated amino acid sequencer.

The modified PAI-1 protein sequence can be characterized by a hydrophilicity analysis (Hopp, T. and Woods, K., 1981, Proc. Natl. Acad. Sci. U.S.A. 78:3824). A hydrophilicity pro-file can be used to identify the hydrophobic and hydrophilic regions of the PAI-1 protein and the corresponding regions of the gene sequence which encode such regions.

Secondary structural analysis (Chou, P. and Fasman, G., 1974, Biochemistry 13:222) can also be done, to identify regions of the PAI-1 protein that assume specific secondary structures.

Other methods of structural analysis can also be employed. These include but are not limited to X-ray crystallography (Engstom, A., 1974, Biochem. Exp. Biol. 11:7-13) and computer modeling (Fletterick, R. and Zoller, M. (eds.), 1986, Computer Graphics and Molecular Modeling, in Current Communications in Molecular Biology, Cold Spring Harbor Laboratory, Cold Spring Harbor, N.Y.).

The functional activity of modified PAI-1 protein molecules can be assayed by various methods known in the art.

For example, where one is assaying for the ability of a modified PAI-1 protein to bind or compete with wild-type PAI-1 proteins for binding to an antibody, uPA, or tPA, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. Antibody binding can be detected by detecting a label on the primary antibody. Alternatively, the primary antibody is detected by detecting binding of a secondary antibody or reagent to the primary antibody, particularly where the secondary antibody is labeled. Many means are known in the art for detecting binding in an immunoassay and are within the scope of the present invention.

In a specific embodiment, the sensitive measurement of functionally active human PAI-1 is easily performed with this 96 well strip format ELISA kit. Functionally active PAI-1 present in plasma or culture media reacts with urokinase provided pre-coated on a micro titer plate. Latent or complexed PAI-1 will not bind to the plate and will not be detected. After appropriate washing steps, anti PAI-1 primary antibody binds to the PAI-1. Excess antibody is washed away, and bound antibody, which is proportional to the original active PAI-1 present in the plasma sample, is then reacted with the secondary antibody conjugated to Alkaline Phosphatase. A standard calibration curve is prepared along with the samples to be measured using dilutions of purified PAI-1 in plasma.

Another specific functional assay for PAI-1 that may be used in the present invention is based on the immobilisation of functional active t-PA to plates by means of t-PA monoclonal antibody. PAI-1 of the test-sample binds to t-PA and is then quantified using a peroxidase-labeled monoclonal anti-PAI-1 antibody. Another specific functional assay for measuring PAI-1 function is the amidolytic assay.

Other functions of PAI-1 include, but are not limited to, binding to uPA, tissue-type plasminogen activator, integrin-alpha-3-beta-2, and vitronectin. In a preferred embodiment, the modified PAI-1 molecule does not bind to tPA. In another preferred embodiment, the modified PAI-1 molecule does not bind to integrin.

The half-life of a protein is a measurement of protein stability and indicates the time necessary for a one-half reduction in the concentration of the protein. The half-life of a modified PAI-1 can be determined by any method for measuring PAI-1 levels in samples from a subject over a period of time, for example but not limited to, immunoassays using anti-PAI-1 antibodies to measure the levels of the modified PAI molecules in samples taken over a period of time after administration of the modified PAI-1 or detection of radiolabelled modified PAI-1 molecules in samples taken from a subject after administration of the radiolabeled modified PAI-1 molecules.

Other methods will be known to the skilled artisan and are within the scope of the invention.

5.7. Therapeutic Uses

The invention provides for treatment, prophylaxis, management or amelioration of one or more symptoms associated with the disease, disorder, or infection by administration of therapeutic compound (termed herein "Therapeutic") of the invention. Such Therapeutics include modified PAI-1 molecules having at least two amino acid substitutions at positions 31 and 97, 192 and 347, or 197 and 355 of the PAI-1 protein as depicted in FIG. 2A (SEQ ID NO:2), preferably with two or more amino acid substitutions at or near the β-sheet. More specifically, the two or more amino acid substitutions are at or near helix D, β-sheet b, and/or β-sheet t. The Therapeutics of the present invention include a modified PAI-1 molecule with mutations at amino acid positions located near or within the β-sheet so that one or more disulfide bridges may be formed that hold the A3 strand and the A5 strand of the β-sheet closer together, thus preventing the insertion of the A4 strand between the A3 strand and the A5 strand of the β-sheet. The Therapeutics of the present invention also include a modified PAI-1 protein in which two or more amino acid residues that do not contain a sulfhydryl group have been replaced with amino acid residues that contain sulfhydryl groups such as, but not limited to, cysteine residues, that form one or more intrachain disulfide bonds, in which the active form has a much longer in vivo half-life than a PAI-1 protein, such as a wild-type PAI-1 protein. Modified PAI-1 molecule comprises amino acid sequence in which two or more amino acid residues other than a cysteine residue or methionine residue are substituted with cysteine residues or methionine residues. The number of amino acid residues that may be substituted in a modified PAI-1 being 1, 2, 3, 4, 5, 6, 7, 8, 9, 10, or more than 10 and less than 20, more than 20, preferably, an even number of amino acid residues are substituted.

According to the invention, the modified PAI-1 molecules have substitutions, deletions or insertions, of two, four, six, or more amino acid residues in the wild type protein.

In one embodiment, the modified PAI-1 molecules have one or more substitutions of amino acid residues relative to the wild-type PAI-1 molecules, preferably, two or more amino acid substitutions in the amino acid residues selected from among residues at positions 10-40, 70-120, 150-220, and 300-400.

In more preferred embodiments, one or more pairs of amino acid residues selected from the pairs Valine 31 and Alanine 97, or Leucine 192 and Valine 347, or Glutamine 197 and Glycine 355 are replaced with cysteine residues. In more preferred embodiments, one or more disulfide bridges are formed at amino acid positions 31 and 97, 192 and 347, or 197 and 355.

The subject to which the Therapeutic is administered is preferably an animal, including but not limited to mammal such as non-primate (e.g., cows, pigs, horses, chickens, cats, dogs, rats, etc.), and a primate (e.g. monkey such as acynomolgous monkey and a human. In a preferred embodiment, the subject is a human. The therapeutics can be utilized for the prevention of a variety of cancers, e.g., in individuals who are predisposed as a result of familial history or in individuals with an enhanced risk to cancer due to environmental factors.

The methods and compositions of the invention may be used in patients who are treatment naive, in patients who have previously received or are currently receiving treatment with other pharmaceutical agents or combinations, including but not limited to anti-cancer agents, antibiotics, anti-bacterial agents, anti-fungal agents and anti-viral agents. Generally, administration of products of a species origin that is the same species as that of the subject is preferred. Thus, in a preferred embodiment, a human modified PAI-1 molecule or nucleic acid encoding such protein molecule is therapeutically or prophylactically administered to a human patient. Other subjects may include patients that have metastasis or no metastasis.

The methods and compositions of the invention are useful not only in untreated patients but are also useful in the treatment of patients partially or completely un-responsive to other treatments. In various embodiments, the invention provides methods and compositions useful for the treatment of diseases or disorders in patients that have been shown to be or may be refractory or non-responsive to therapies comprising the administration of other agents.

The Therapeutics can also be administered to an animal, preferably a mammal, and most preferably a human, to treat, prevent or ameliorate one or more symptoms associated with the disease, disorder, or infection related to abnormal angiogenesis, inflammation, or cancer.

The present invention provides Therapeutics for the treatment, prophylaxis, management or amelioration of one or more symptoms associated with the disease, disorder, or infection. These diseases, disorders, or infection manifest as cell proliferation, hyper-angiogenic diseases, psoriasis or inflammatory diseases. Disorders in which PAI-1 is absent or decreased relative to normal or desired levels are treated, prevented, managed, or ameliorated by administration of a modified PAI-1 molecule of the invention. Also, disorders that are related to increased uPA, or tPA relative to normal levels may also be treated, prevented, managed, or ameliorated by the methods of the invention.

The absence of decreased level in PAI-1 protein or function can be readily detected, e.g., by obtaining a patient tissue sample (e.g., from biopsy tissue) and assaying it in vitro for RNA or protein levels, structure and/or activity of the expressed RNA or protein of PAI-1. Many methods standard in the art can be thus employed, including but not limited to immunoassays to detect and/or visualize PAI-1 protein (e.g., Western blot, immunoprecipitation followed by sodium dodecyl sulfate polyacrylamide gel electrophoresis, immunocytochemistry, etc.) and/or hybridization assays to detect PAI-1 expression by detecting and/or visualizing PAI-1 mRNA (e.g., Northern assays, dot blots, in situ hybridization, etc.), etc.

In specific embodiments, Therapeutics of the invention are used to treat cancer. The modified PAI-1 molecules are useful in decreasing invasion and metastatic.

In other specific embodiments, the modified PAI-1 of the invention can be used for targeted delivery of toxins such as, but not limited to, ricin, diptheria toxin, etc.

5.8. Pharmaceutical Compositions

The invention provides methods of treatment, prophylaxis, management, or amelioration by administration to a subject of an effective amount of a Therapeutic of the invention. In a preferred aspect, the Therapeutic is substantially purified. The subject is preferably an animal, including but not limited to animals such as cows, pigs, horses, chickens, cats, dogs, etc., and is preferably a mammal, and most preferably human. In a specific embodiment, a non-human mammal is the subject.

The modified PAI-1 protein molecules of the invention are preferably tested in vitro, and then in vivo for the desired, prior to use in humans. In various specific embodiments, in vitro assays can be carried out with representative cells of cell types (e.g., thyroid cells) involved in a patient's disorder, to determine if a modified PAI-1 protein molecule has a desired effect upon such cell types.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used.

Various delivery systems are known and can be used to administer a modified PAI-1 protein molecule of the invention, e.g., encapsulation in liposomes, microparticles, microcapsules, recombinant cells capable of expressing the modified PAI-1 protein molecule receptor-mediated endocytosis (see, e.g., Wu and Wu, 1987, J. Biol. Chem. 262:4429-4432), etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, by means of a catheter, by means of a suppository, or by means of an implant, said implant being of a porous, non-porous, or gelatinous material, including membranes, such as sialastic membranes, or fibers.

In another embodiment, the modified PAI-1 protein molecules can be delivered in a vesicle, in particular a liposome (see Langer, 1990, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the modified PAI-1 protein molecules can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, thus requiring only a fraction of the systemic dose (see, e.g., Goodson, in Medical Applications of Controlled Release, supra, vol. 2, pp. 115-138 (1984)).

Other controlled release systems are discussed in the review by Langer, 1990, Science 249:1527-1533 (1990). Other method of delivery of the therapeutics of the present invention may be used for example, as described in U.S. Pat. No. 5,679,350, which is incorporated by reference in its entirety.

In a specific embodiment, a nucleic acid encoding modified PAI-1 protein molecules can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid molecule encoding a modified PAI-1 protein molecule can be introduced intracellularly and incorporated within host cell DNA for expression, by homologous recombination.

The present invention also provides pharmaceutical compositions. Such compositions comprise a therapeutically effective amount of a modified PAI-1 protein molecule and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the modified PAI-1 protein molecules preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The modified PAI-1 protein molecules of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the modified PAI-1 protein molecules of the invention which will be effective in the treatment of a particular disorder or condition will depend on the nature of the disorder or condition, and can be determined by standard clinical techniques. In addition, in vitro assays and animal models may optionally be employed to help identify optimal dosage ranges. The precise dose to be employed in the formulation will also depend on the route of administration, and the seriousness of the disease or disorder, and should be decided according to the judgment of the practitioner and each patient's circumstances.

In specific embodiments, the Therapeutics of the invention are administered intramuscularly. Suitable dosage ranges for the intramuscular administration are generally about 10 µg to 1 mg per dose, preferably about 10 µg to 100 µg per dose. In one embodiment, the Therapeutic is administered in two doses, where the second dose is administered 24 hours after the first dose; in another embodiment, the Therapeutic is administered in three doses, with one dose being administered on days 1, 4 and 7 of a 7 day regimen.

Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pack or kit for therapeutic use comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or diagnostic products, which notice reflects approval by the agency of manufacture, use or sale for human administration.

5.9. Characterization and Demonstration of Therapeutic or Prophylactic Utility Toxicity and efficacy of the prophylactic and/or therapeutic protocols of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The anti-cancer activity of the therapies used in accordance with the present invention also can be determined by using various experimental animal models of such as cancer animal models such as scid mouse model or nude mice with human tumor grafts known in the art and described in Yamanaka, 2001, Microbiol Immunol 2001; 45(7):507-14. For angiogenesis and tumor mouse model that are used in the present invention are discussed in Section 6.12.7 below.

The protocols and compositions of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which a patient tissue sample is grown in culture, and exposed to or otherwise administered a protocol, and the effect of such protocol upon the tissue sample is observed. A lower level of proliferation or survival of the contacted cells indicates that the Therapeutic is effective to treat the condition in the patient. Alternatively, instead of culturing cells from a patient, Protocols may be screened using cells of a tumor or malignant cell line. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc.

Compounds for use in therapy can be tested in suitable animal model systems prior to testing in humans, including but not limited to in rats, mice, chicken, cows, monkeys, rabbits, etc.

The principle animal models for cancer known in the art and widely used include mice:, all described in Hann et al., 2001, Curr Opin Cell Biol 2001 December; 13(6):778-84, which is incorporated herein by reference in its entirety.

Further, any assays known to those skilled in the art can be used to evaluate the prophylactic and/or therapeutic utility of the combinatorial therapies disclosed herein for treatment or prevention of cancer.

Efficacy in treating inflammatory disorders may be demonstrated by detecting the ability of the modified PAI-1 molecules of the present invention, or a composition of the invention to reduce or inhibit the inflammation in an animal or to ameliorate or alleviate one or more symptoms associated with an inflammatory disorder. The treatment is considered therapeutic if there is, for example, a reduction is in inflammation or amelioration of one or more symptoms following administration of the modified PAI-1 molecules, or a composition of the invention. Sprout formation assay as discussed in Section 6.12.1 and Section 6.12.4 may be used to measure anti-angiogenic activity on human umbilican vein endothelial cells as a human cell model. In addition, the chicken chorioallantoic membrane (CAM) assay may also be used to measure angiostatic effect of a compound. The following examples are provided as illustrations and not by limitation.

6. EXAMPLES

Plasminogen activator inhibitor type 1 (PAI-1), which blocks uPA proteolysis, is capable of reducing tumor growth, and to impair metastasis. Because of the high affinity to uPA and the apparent lack of toxicity, it can serve as an anti-cancer agent. However, wild PAI-1 converts into its latent, non-active form in very short time (½-2 hours). The following examples shows that modified PAI-1 protein of the present invention in which the latent form has extended half-life (6.7 days) is a potent anti-angiogenic agent.

6.1. Purification of PAI-1 with Extended Half-life from pTYB12-PAI Vector

As shown in FIG. 7, the human PAI-1 1B-14 mutant cDNA was excised from pQE30-PAI-1 vector as a NdeI/NsiI fragment and separated from pQE30 vector by DNA agarose gel electrophoresis. The PAI-1 1B14 mutant cDNA was further cut to NdeI/PstI fragment and removed from gel by electroelution. This fragment was then ligated using T4 DNA ligase into NdeI/PstI-cut pTYB-12 vector to create pTYB12-PAI1 vector and transformed into E. coli strain ER567 by rubidium chloride ($RbCl_2$) precipitation. Transformed cells were seeded on nutrient agar plates containing ampicillin (100 µ/ml) and grown overnight at 37° C.

A single colony was transferred to a test tube containing 6 ml of LB-broth and ampicillin and grown overnight. On the following day, pTYB12-PAI-1 plasmid DNA was isolated using the alkaline lysis method. Purified plasmid DNA was subjected to restriction analysis to determine that 1B-14 cDNA was incorporated into pTYB12 vector by double digestion with NdeI and BlpI restriction enzymes. Finally, pTYB12-PAI-1 plasmid DNA was transformed by rubidium chloride precipitation into ER2566 E. coli strain, which was T7 polymerase gene incorporated into its genome.

One liter of fresh LB broth medium containing ampicillin was inoculated with freshly grown culture and was incubated at 37° C., until the $OD_{600}$ of the cell culture reached 0.6. The expression of the 1B-14 mutant of human PAI-1 was stimulated by addition of IPTG to a final concentration of 0.5 mM. Next, cells were spun down, the cell pellet was washed with 50 ml ice cold Cell Lysis Buffer (20 mM NA-HEPES, 500 mM Nalco, 1 mM EDTA, 20 µM PMSF, 5 mM $MgCl_2$, 10 µ/ml protease-free Dane; pH=8.00). After washing, cells were resuspended in 30 ml of Cell Lysis Buffer and broken down in a French press. The cell debris was removed by centrifugation and clear crude cell extract was transferred to a new tube and stored in the freezer at −20° C.

PAI-1 1B14 mutant was isolated on intein binding column. In this protocol, 30 ml of chitin bead resin was equilibrated with 10 bed volumes of Column Buffer (20 mM HEPES, 500 mM Nalco, 1 mM EDTA; pH—8.00). Crude cell extract from 1 liter of cell culture was slowly applied onto chitin bead column at a 0.5 ml/min flow rate. In the next step, the column was extensively washed with 20 bed volumes of column buffer at 1.0 ml/min flow rate to remove unbound proteins. Next, the column was fast flushed with 3 bed volumes of Cleavage Buffer (20 mM HEPES, 500 mM Nalco, 1 mM EDTA, 50 mM DTT; pH=8.00) at 2.0 ml/min and incubated for 40 h at 4 EC to stimulate on-column cleavage. The released from intein purification tag PAI-1 1B14 mutant was eluted from the column with Column Buffer. The eluted PAI-1 was dialyzed overnight against PBS Buffer (120 mM Nalco, 2.7 mM KCl, 10 mM $Na_3PO_4$; pH 7.40) and concentrated. The purity of PAI-1 1B14 mutant was estimated as +95% as tested by SDS-PAGE. Yield was approximately 15-20 mg/l of cell culture. Activity of PAI-1 was verified by amidolytic assay.

6.2. Modified PAI-1 Molecules

A total of seven cysteine mutants have been created via point mutation (two, four, and six point mutations) generating possible sites for disulfide bridge formation at the top and bottom parts of A3 and A5, within the helix D region, or by a combination thereof. Modified PAI-1 was expressed using a bacterial expression vector, pTYB12, producing a fused PAI-1/intein tag. The modified forms of PAI-1 containing the chitin binding intein tag were then purified using affinity chromatography wherein the intein tag is cleaved leaving modified PAI-1 protein. Approximate protein yield was 1-5 mg/L of cell culture. The cysteine mutations appear to have no detrimental effects on enzymatic activity but can increase the $t_{1/2}$ of modified PAI-1 when compared to wild-type PAI-1. Among the mutants tested thus far, the longest $t_{1/2}$ (96 hrs) was observed in the species containing combined mutations (4 point mutations) in A3 and A5 (bottom; Leu192, Val347) as well as within the helix D region (Val31, Ala97). In comparison, mutations that denote rigidity to the helix D region only (2 point mutations), which restricts movement of the reactive loop in this region, produced protein with a shorter $t_{1/2}$ (12 hr). These results indicate that by introducing cysteine residues into PAI-1, which are absent in the wild-type species, the $t_{1/2}$ of PAI-1 can be extended to therapeutically desired values. Table 1 shows the half-life of PAI-1 mutants generated in the present invention.

TABLE 1

| PAI-1 Mutations | Half life in hours |
|---|---|
| Wild-type | 1.5 |
| helix D | 11 |
| helix D and β-sheet b | 73 |
| helix D and β-sheet t | 61 |
| helix D and β-sheet tb | 6 |
| β-sheet tb | 96 |
| β-sheet b | 165 |
| β-sheet t | >220 (after 220 h ~98% active) at 720 hours, 95% active. |

6.3. Amidolytic Assay of Anti-uPA Activity

Tris (50mM) with 0.01% Tween 80, 0.01% PEG 8000 (pH 8.8) and 10 KIU/ml sterile aprotinin (Sigma Chemical Co., St. Louis, Mo.) was incubated with 1 μg of uPA and decreasing amounts of inhibitor (initially 100 μg/ml) for 15 minutes; 100 μl of this mixture was incubated in 96-well microplates with 50μl of 2.5 mM SPECTROZYME® UK (Cbo-L-(γ)-Glu (α-t-BuO)-Gly-Arg-pNA.2AcOH), (American Diagnostica Inc., Greenwich, Conn.), for 15 mins. Absorbance at 405 nm was read on a microplate reader. Absorbance is inversely proportional to the uPA inhibitory activity.

6.4. tPA and PAI-1 Assays

SPECTROLYSE® IPA/PAI, Product # 452, is a single-step, indirect enzymatic assay intended for the determination of fibrinolytic activity exerted by tissue plasminogen activator (tPA). The assay is primarily intended for determinations of IPA activity and IPA inhibitor levels (PAI) in human plasma samples, but it can be adapted for tPA and PAI determinations in most biological fluids (eg, lymph and synovial fluids) as well as cell culture supernatants and animal plasmas.

The SPECTROLYSE® tPA/PAI assay is based on the functional parabolic rate assay described by Ránby[1] aild its adaptation to plasma samples as described Wiman[2]. It is a rapid and convenient assay utilizing a final mixture containing sample, plasminogen, fibrin and a plasmin substrate. tPA in the sample activates the plasminogen to plasmin. The plasmin cleaves the plasmin substrate generating a yellow colored solution. The absorbance of the solution measured at 405 nm is a quantitative measure of the IPA activity in the sample. Use of the unique fibrin stimulator DESAFIB® and the highly efficient plasmin substrate SPECTROZYME® PL together provide a highly sensitive, selective and single-tube assay.

Reagents: Human Glu-plasminogen, lyophilized; DESAFIB®-X: lyophilized; SPECTROZYME® PL: lyophilized; tPA Standard, 2-chain:lyophilized; TRIS Buffer; Acetate Buffer; Stop Solution. (contains SDS).

6.4.1. Determination of tPA Activity of Blood Plasma

Add 100 μL Acetate buffer to 200 μL freshly drawn blood. This acidification should be done within 15 seconds of collection to prevent IPA from complexing with PAI and causing artificially low tPA activity levels. Centrifuge the blood sample at 2000 g for 5 minutes (within 15 minutes of acidification to avoid hemolysis). Pipette 100 μL of supernatant (acidified plasma) to a new tube and add 100 μL acetate buffer and 100 μL TRIS Buffer. Incubate at 37° C. for 20 minutes (to destroy alpha-2-antiplasmin which interferes with the assay). SPECTROLYSE® tPA/PAI can be applied to previously frozen plasma samples providing they were acidified prior to freezing. When frozen at −80° C., tPA activity is stable for several months[2]. Any precipitate observed upon thawing appeals to have no effect on tPA activity. For Cell Culture Supernatants, follow the first step and filter the supernatant using a 0.22 micron low protein binding membrane to remove any cell debris.

6.5. Preparation of Standards for Standard Curve

Note the labeled activity of the tPA Standard (ADI Product #116). For example, if the tPA standard after reconstitution was diluted to 10 IU/mL (final concentration), dilute further as follows with TRIS Buffer to obtain 6 standard points:

| tPA Concentration (IU/mL) | Vol. TRIS (µL) | Vol. tPA Standard (µL) |
|---|---|---|
| 0.0 | 1000 | 0 |
| 0.2 | 980 | 20 |
| 0.5 | 950 | 50 |
| 1.0 | 900 | 100 |
| 2.0 | 800 | 200 |
| 3.0 | 700 | 300 |

Added 500 µL of "TAR" to each small centrifuge tube. Add 20 µL of either standard or test sample to each tube. The "0.0 IU/mL" standard serves as the blank. Add 20 µL of DESAFIB®. After addition mix immediately and place each tube in the 37° C. water bath. Incubate at 37° C. for 75 minutes. For increased sensitivity to measure tPA activity within the range of 0.0 IU/mL to 0.3 IU/mL (for example), standards may be diluted an additional 100 fold with TRIS Buffer and the incubation time extended to 20 hours. Add 50 µL Stop Solution to each tube. Mix well. Centrifuge at 5000 g or more for 30 seconds (skip this step for microtitre plate format). Read the solution absorption at 405 nm ($A_{405}$) within 30 minutes. Subtract the $A_{405}$ of the blank from all absorbance values. Note the difference as $\Delta A_{405}$. Construct a standard curve by plotting the $\Delta A_{405}$ of each standard versus its tPA concentration. Assess the tPA content of each test sample by interpolating the concentration directly from the standard curve. A standard curve should be generated each time the assay is performed. Reagents have been titred in this assay to generate a standard curve from $A_{405}$ of 0 to 1.0. Using the mean absorbance value for each diluted test sample, determine the corresponding tPA activity in IU/mL from the generated standard curve. To obtain an exact determination of the tPA activity in plasma, multiply by the dilution factor:

$$(tPA)_{diluted\ sample} \times \frac{3[100 + 200(1 - Hc)]}{[200(1 - Hc)]} = [tPA]_{sample}$$

Where $H_c$=average hematocrit of the blood sample. For example, if the $H_c$=0.45, the dilution factor is 5.7. If you wish to report the results as tPA activity in whole blood, use $H_c$=0, so that the dilution factor is 4.5.

6.6. Expected tPA Activity Values

The tPA activity level in mammalian plasma varies greatly. The basal (resting) levels of tPA range from 0.0-0.04 IU/IL in normal patients and from 0.0-0.85 IU/mL for DVT patients. Following venous occlusion, exercise stress, and desmopression infusion, tPA levels have been reported to range from 1.4-14 IU/mL for normal patients and 0.0.-25 IU/mL for DVT patients. Wilman et al., 1985, J. Lab Clin Med 105:265-270. Owing to these wide ranges of reported valves, it is recommended that venous occlusion, exercise, and desmopression samples be measured using a 2 hour, 37° C. incubation and that basal level samples be measured using a 20 hour, 37° C. incubation.

6.7. Determination of PAI Levels in Blood Plasma

The SPECTROLYSE® tPA/PAI assay is suitable for determination of tPA inhibitor, PAI. The inhibitor level is determined as the difference between the amount of tPA activity added to the plasma sample and the amount of tPA activity remaining after a defined period of time. Wilman et al., 1984, J. Biol Chem 259:3644-3647. PAI analysis can be performed on citrated (STABILYTE™ tube), EDTA or heparinized plasma. Alternatively, acetate prepared plasma as described in Part I, SAMPLE COLLECTION AND PREPARATION, A. Plasma, Steps 1 and 2 on page 3 of this insert may be used. (Do not add additional Acetate arid TRIS Buffer as described In Step 3). Remember to record the dilution factor of the patient blood for later calculations.

6.8. Preparation of Standards for Standard Curve

Use the same standards as described in section 6.5. Dilute test sample 1: 2 with TRIS Buffer. Add 100 µL of diluted test sample to 100 µL of (PA activity standard and incubate for 15 minutes at room temperature. This allows for the tPA and PAI to react and complex. As described earlier, a 10 IU/mL tPA standard will be used for example. Note the tPA activity on the vial label and the subsequent activity level of the stock solution generated. Add 250 µL Acetate buffer to the sample and incubate at 37° C. for 15 minutes (to destroy alpha-2-anti-plasmin which would otherwise interfere with the assay). At this point, the sample contains a maximum of 2.22 IU/mL of tPA activity if no PAI were present in the plasma. Prepare a "0 PAM" as follows: Add 250 µL Acetate buffer, 100 µL test sample diluted 1:2 with TRIS and 100 µL of 10 IU/mL tPA standard to a tube and incubate at 37° C. for 15 minutes (destroys alpha-2-anti.plasmin). The tPA and the PAI-1 have not reacted in this "0 PAM" because of the low pH of the mixture. Prepare a "Blank" as follows: Add 250 µL Acetate, 100 µL normal plasma (or fresh cell culture media) diluted 1:2 and 100 µL TRIS Buffer to a tube. Incubate at 37° C. for 15 minutes. ("Blank" has no added tPA activity). Assay the "0 PAI", "Blank". Determine the residual tPA activity in the "0 PAI", the "Blank" and the sample, using the Standard Curve generated as described in Part I of this insert. The PAI content of the sample is calculated by taking the difference between the "0 PAI" and the sample and multiplying by 4.5 (dilution factors of plasma with reaction volume) and then by 2 (dilution of plasma prior to assaying).

$$[PAI] = 4.5 \times 2 \times (C_o - C_5)$$

[PAI]=PAI content in plasma
$C_0$=tPA content in "0 PAI" (should by approximately 2.2 IU/mL)
$C_5$=tPA content in sample tube

6.9. Assay Conditions/SubstrateKinetics for SPECTROZYME® UK

Enzyme activity is determined by measuring the increase in absorbance of the free chromophore (pNA) generated per unit time at $\lambda_{405}$ nm. At excess substrate concentrations, the rate at which the absorbance increases due to the amount of chromophore released is linearly related to enzyme concentration. Measurement can be made either through acid quenching of the reaction (end-point method), or through use of a kinetic recording spectrophotometer (initial-rate-method). Under the following reaction conditions, the following substrate kinetics were found,

| Buffer: | 0.05 M Tris pH 8.8, pH 37° C. | | |
|---|---|---|---|
| Substrate: | 0.5 mM No. 244 | | |
| Enzyme: | urokinase at 1000 u/mL | $K_m$ | $V_{max}$ |
| HMWt, Choay: | | 30 µM | 0.54 µM mm$^{-1}$ |
| LMWt, Abbott: | | 80 µM | 0.53 µM mm$^{-1}$ |

Harvey, S. R., et al., 1988, Clin Expl Metastasis 6(6): 431–450.

6.10. Urokinase Activity Determination Direct Assay 50 mM Tris with 0.01% Tween 80 or 0.1% PEG 8000 and 10 KIU/mL sterile aprotinin (ADI Product No. 515 or 517), pH 8.8. SPECTROZYME® UK at 2.5 mM concentration (ADI Product No. 244 or 244L). To a micro-test plate (37° C.) wells add: 50 μL of buffer, 50 μL of filtered sample (free of particulate and colored matter), or UK standards or controls, and 50 μL of SPECTROZYME® UK Mix and incubate 15 minutes at room temperature or 3 minutes at 37° C. Read the absorbance on a micro-plate reader (405 nm) or repeatedly during the following 10 minutes:

The lower limit of detection of this direct urokinase assay is approximately 20 IU/mL. Sensitivity is estimated to be 4-5 IU/mL of sample. A standard curve can be prepared using Products No. 124 or No. 125, (HMW and LMW urokinase activity standards, respectively).

6.11. Urokinase Activity Determination—Indirect Assay 50 mM Tris with 0.01% Tween 80 or 0.1% PEG 8000, pH 7.4. SPECTROZYME® PL at 0.4 mM concentration (ADI Product No. 251). Add 6 mM EACA (6-aminohexanoic acid) and 0.1 mg/mL Bovine Plasminogen (ADI Product No. 416) to the buffer. Follow protocol listed above for the Direct Assay. The assay sensitivity is estimated to be 10-100 fold higher than the direct assay. The incubation time must be monitored as there is a definite risk of activation of pro-UK (scu-PA) by the plasmin formed. Urine samples exhibit absorbance at 405 nm (approximately 0.100 OD for a 10% urine solution). Urine samples must be diluted with buffer prior to assay to reduce the background signal. Alternatively, measure this background absorbance and deduct the value from the sample readings.

6.12. Anti-angiogenic Activity of PAI-1 with Extended Half-Life

6.12.1. Sprout Formation Assay

Sprout formation assay was performed using human endothelial cells to determine anti-angiogenic activity of PAI-1. These cells express high activity of uPA on the tip of the sprout when grown in fibrin gels. Inhibition of uPA will prevent sprout formation and will be a measure of anti-angiogenic activity on the human cell model.

6.12.2. Preparation of Human Umbilican Vein Endothelial Cells (HUVEC) Aggregates HUVEC were grown to confluence in EGM-2 growth medium. Cells were trypsinized and seeded onto 0.5% agarose coated culture dishes. This procedure resulted in cells aggregate formation after 24 h of incubation at +37° C. The HUVEC aggregates were decanted under gravitational force by allowing the cells to stand for 30 min. at room temperature. The old-medium supernatant was decanted and HUVEC aggregates were suspended in 5 ml of fresh EGM-2 growth medium.

6.12.3. Preparation of Three-dimensional Fibrin Gel

Three-dimensional fibrin gels were prepared by mixing the following in 12-well culture plates: 960 μl of human fibrinogen (Type III, 60% of protein clottable; 2.50 mg/ml concentration in RPMI-1640 medium), 40 μl of HUVEC aggregate suspension, and 12.5 μl of human thrombin (25 IU/ml concentration in RPMI-1640 medium). The mixture was gently mixed and allowed to gel for about 4 minutes at +37° C. before adding EGM-2 growth medium over the gel.

6.12.4. Sprout Formation Assay for HUVEC

The HUVEC aggregates were suspended in fibrin gel containing benzamidine (31 μM), B428 (40 nM) and 1B-14 PAI-1 mutant; 1 ml of EGM-2 growth medium was added over the fibrin gel. The PAI-1 in the fibrin gel was adjusted to a final concentration of 0.50, 0.75, 1.00, 2.00, 3.00; 4.00, and 5.00 μM. The 1B-14 PAI-1 mutant solution used in this study was dialyzed against PBS Buffer (pH=7.40) overnight at +4° C. After 3 days of cell incubation, cultures were fixed in situ for 24 h with 2 ml of 10% formalin solution and photographed under a phase-contrast microscope as shown in FIGS. 8A and 8B.

6.12.5. Chicken Chorioallantoic Membrane (CAM) Assay

This is a secondary and independent assay of antiangiogenic activity of PAI-1 with extended half-life. The one-day-old fertilized eggs were incubated for three days in the water-jacketed incubator (38° C., 85% humidity). The eggs were cracked and the chick embryos with intact yolks were placed in plastic Petri dishes containing 10 ml of RPMI-1640 medium (38° C., 85% humidity, 3% of CO2). After 3 days of incubation, the methylcellulose disk containing inhibitor was implanted on the CAMs of the individual embryos. After 48 h of incubation, CAM of individual embryo was analyzed for formation of avascular zones and photographed. The angiostatic effect was determined as a percentage of the area of blood vessels under the methylcellulose disks (3-5 eggs for each concentration) in relation to the non-treated areas.

All urokinase inhibitors tested reduce angiogenesis in the chick embryos in concentration dependent manner. In case of epigallocatechin gallate ("EGCG"), which possesses antioxidant activity, the methylcellulose disks quickly change color. EGCG produce colorless or yellowish solution and the change of color to brown is a sign of a probable oxidation of this chemical. Therefore, inhibition of angiogenesis in this instance could be affected by these changes. Formation of embryonic neovascularization was significantly reduced under the methylcellulose disks in all cases as shown in FIG. 9. Additionally, angiogenesis was observed in the large avascular zones outside of areas covered by methylcellulose disk containing the inhibitor. The effect was observed for B428 and amiloride. In contrast, the control CAMs implanted on the empty methylcellulose disks without inhibitors did not develop avascular zones as determined by visual examination (FIG. 9A). As the positive control, methylcellulose disk containing VEGF was implanted and dense areas of newly formed vessels were developed. The percentage of area covered by blood vessels were presented in FIG. 10.

6.12.6. Image Processing and Analysis

The area below the dialysis bag and two non-treated areas were scanned and saved on computer disk as tif files. Color images were converted into black/white images, contrast was enhanced, and images were saved as 16-bitmap files using Paint Software (Microsoft Corporation, Redmond, Va.). Black/white images were converted into false color (rainbow striped) images using Transform2 Software (Fortner, Sterling, Va.). Finally, the area of the blood vessels was calculated using T3D Software (Fortner, Sterling, Va.). This method provides some quantification of angiogenesis.

6.12.7. The Animal Model of Tumor Progression

50 SCID/BALB-c mice (males) were subcutaneously inoculated in the left rear flank with $1.0 \times 10^6$ cells of LNCaP expressing undetectable amounts of u-PA. After 30 days when the tumor was 3 mm in diameter, animals were divided into 6 groups. Control-1 group (n=8) composed of SCID-mice inoculated with LNCaP tumor cells. Control-2 group (n=8) composed of SCID-mice inoculated with LNCaP cells and receiving saline solution delivered via ALZET® osmotic pump. There were 4 treatment groups (n=8, each) composed of SCID-mice inoculated with LNCaP tumor cells and receiving 1B-14 human PAI-1 mutant solution at concentrations of $5.00 \times 10^{-10}$ M, $2.50 \times 10^{-9}$ M, $5.00 \times 10^{-9}$ M, and $10.00 \times 10^{-9}$ M, respectively. The PAI-1 solution was delivered via an ALZET® osmotic pump.

A 200 µL (model #2004) osmotic pump was used and the 1B-14 human PAI-1 mutant and saline solutions were delivered at a flow rate of 0.25 µL/h. Tumor size in each group was measured every 3 days over the 28-day course of the experiments and the volume was calculated using the following formula:

$$V = 4/3 \cdot \Pi \cdot R_1^2 \cdot R_2$$

Where: V=volume [cm³]; $R_1$=radius; $R_2$=radius; and $R_1 > R_2$

The result of this experiment is shown in FIG. 11.

In this experiment it was a single application of PAI-1 that gradually converted itself into latent, not active form. In the end of experiment only less than 6% of original activity remain as it is shown in FIG. 12.

6.13. Discussion

An increased amount or activity of uPA or uPAR per cell has been found in human cancer cells lines with metastatic behavior. Festuccia et al., 1995, Oncology Res. 7(3-4): 131-138. Animals injected with cancer cells expressing higher amounts of uPA and/or uPAR develop metastatic lesions earlier and more frequently than animals injected with the same cell expressing lower amounts of uPA/uPAR. Achbarou et al., 1994, Cancer Research 54(9):2372-2377. Additionally, uPA activity is increased in metastatic tumors compared with primary tumors in experimental animals. Wilson et al., Cell. Mol. Biol. Res., 1989, 39(8): 751-760. The ability of human carcinoma cells to metastasize to chick embryo was dramatically reduced when cells were treated with the antibody against the active site of uPA. Ossowski et al., 1988, J. Cell Biol. 107:2437-2445. Prostate cancer cells transfected with a plasmid overexpressing of uPA in prostate cancer cells showed a marked increase in metastasis, in comparison with the parental cell phenotype in the rat model. Cells from the same phenotype underexpressing uPA displayed drastically decreased metastasis. Achbarou et al., 1994, Cancer Research, 54(9):2372-2377. The other plasminogen activator tPA, is rarely overexpressed in malignant tumors and does not seem to be relevant in the metastatic process. Jankun et al., 1997, Cancer Research 57:559-563.

The mechanism of action leading to a decline in tumor growth rate is not clear. Proteolysis is responsible for degradation of proteins, for invasion or metastasis, but not for the proliferate properties of cancer cells. Inhibitors of uPA may be interacting with elements of the extracellular matrix, that express uPA. For example, the neovascular bed surrounding tumors has been reported to contain high amounts of uPA and its receptor. Pepper et al., 1985, J. Cell Biol. 105:2535-2541. Binding of proteolytically inactive ligands to uPA receptor reduces the amount of uPA on the surface of capillary endothelial cells and reduces tumor growth. Pepper et al., 1993, J. Cell Biol. 122:673-676. Indeed, uPA inhibitors decrease angiogenesis in the chicken embryo model. Swiercz et al., 1999, Oncology Reports 6:523-526.

Inhibitors of urokinase limit cancer growth by inhibiting angiogenesis. However, uPA inhibitors can act on cancer cells directly or prevent angiogenesis by an alternative mechanism not related to uPA inhibition.

The present invention is not to be limited in scope by the microorganism deposited or the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties. Citation of references hereinabove shall not be construed as an admission that such references are prior art to the present invention.

REFERENCES

Rânby et al., 1982, Thrombosis Research 27:743-749.
Wiman et al., 1983, Clin. Chem Acta 127:279-288.

---

What is claimed is:

1. A modified plasminogen activator inhibitor type-1 (PAI-1) molecule comprising an amino acid sequence that is at least 95% identical to the amino acid sequence of SEQ ID NO:2, in which one or more amino acid residues are each substituted by an amino acid residue that contains a sulfhydryl group, such that one or more disulfide bridges are formed at a position selected from the group consisting of 31, 97, 192, 197, 347, and 355 of SEQ ID NO:2, wherein said modified PAI-1 molecule has a half-life that is longer than the half-life of a corresponding wild-type PAI-1 molecule, and wherein said modified PAI-1 molecule inhibits urokinase plasminogen activator.

2. The modified PAI-1 molecule of claim 1, which has a half-life of 3 hours, 6 hours, 10 hours, 20 hours, 50 hours, 60 hours, 70 hours, 90 hours, 100 hours, 150 hours, 200 hours, 10 days, 12 days, 16 days, 30 days, or 60 days.

3. The modified PAI-1 molecule of claim 1, wherein said residue that contains a sulfhydryl group is cysteine.

4. A modified plasminogen activator inhibitor type-1(PAI-1) molecule comprising the amino acid sequence of SEQ ID NO:2, except for substitution by an amino acid residue that contains a sulfhydryl group at one or more of positions 31, 97, 192, 197, 347, or 355 of SEQ ID NO:2, wherein said modified PAI-1 molecule has a half-life that is longer than the half-life of a corresponding wild-type PAI-1 molecule, and wherein said modified PAI-1 molecule inhibits urokinase plasminogen activator.

5. A modified plasminogen activator inhibitor type-1 (PAI-1) molecule comprising the amino acid sequence of SEQ ID NO:2, except for substitution by an amino acid residue that contains a sulfhydryl group at positions (i) 31 and 97 of SEQ ID NO:2; (ii) 192 and 347 of SEQ ID NO:2;( iii) 197 and 355 of SEQ ID NO:2; (iv) 31, 97, 192, and 347 of SEQ ID NO:2;(v) 31, 97, 197, and 355 of SEQ ID NO:2; (vi) 192, 197, 347, and 355 of SEQ ID NO:2; or (vii) 31, 97, 192, 197, 347, and 355 of SEQ ID NO:2, wherein said modified PAI-1 molecule has a half-life that is longer than the half-life of a corresponding wild-type PAI-1 molecule, and wherein said modified PAI-1 molecule inhibits urokinase plasminogen activator.

6. The modified PAI-1 molecule of claim 1, wherein said molecule inhibits tissue plasminogen activator.

7. The modified PAI-1 molecule of claim 1, wherein said molecule augments endogenous PAI-1 function.

8. A method of producing a modified plasminogen activator inhibitor type-1 molecule said method comprising:
   (a) introducing into a cell a nucleic acid molecule encoding a modified PAI-1 molecule comprising and amino acid sequence that is at least 95% identical to the amino acid sequence of SEQ ID NO:2, in which one or more amino acid residues are each substituted by an amino acid residue that contains a sulfhydryl group, such that one or more disulfide bridges are formed at a position selected from the group consisting of 31, 97, 192, 197, 347, and 355 of SEQ ID NO:2 , wherein said modified PAI-1 molecule has a half-life that is longer than the half-life of a corresponding wild-type PAI-1 molecule and wherein said modified PAI-1 molecule inhibits urokinase plasminogen activator; and
   (b) culturing the cell under conditions suitable for expression of the modified PAI-1 molecule.

9. A method of producing a modified plasminogen activator inhibitor type-1 (PAI-1) molecule, said method comprising:
   (a) introducing into a cell a nucleic acid molecule encoding a modified PAI-1 molecule said molecule comprising the amino acid sequence of SEQ ID NO:2, except for substitution by an amino acid residue that contains a sulfhydryl group at positions 31, 97, 192, 197, 347, or 355 of SEQ ID NO:2, wherein said modified PAI-1 molecule has a half life that is longer than the half-life of a corresponding wild-type PAI-1 molecule, and wherein said modified PAI-1 molecule inhibits urokinase plasminogen activator; and
   (b) culturing the cell under conditions suitable for expression of the modified PAI-1 molecule.

10. A method of producing a modified plasminogen activator inhibitor type-1 (PAI-1) molecule, said method comprising:
   (a) introducing into a cell a nucleic acid molecule encoding a modified PAI-1 molecule, said molecule comprising the amino acid sequence of SEQ ID NO:2, except for substitution by an amino acid residue that contains a sulfhydryl group at positions (i) 31 and 97; (ii) 192 and 347; (iii) 197 and 355; (iv) 31, 97, 192, and 347; (v) 31, 97, 197, and 355; (vi) 192, 197, 347, and 355; or (vii) 31, 97, 192, 197, 347, and 355, wherein said modified PAI-1 molecule has a half life that is longer than the half-life of a corresponding wild-type PAI-1 molecule, and wherein said modified PAI-1 molecule inhibits urokinase plasminogen activator; and
   (b) culturing the cell under conditions suitable for expression of the modified PAI-1 molecule.

11. A method of treating aberrant angiogenesis in a subject in need thereof, said method comprising administering to the subject an effective amount of the modified PAI-1 molecule of claim 1.

12. A method of treating cancer in a subject in need thereof, said method comprising administering to the subject an effective amount of the modified PAI-1 molecule of claim 1.

13. The method of claim 12, wherein said cancer is selected from the group consisting of breast cancer, colon cancer, ovarian cancer, lung cancer, prostate cancer, melanoma, leukemia, lung cancer, skin cancer, pancreatic cancer, bladder cancer, sarcoma, and uterine cancer.

14. A method of treating urokinase plasminogen activator-mediated fibrinolysis in a subject in need thereof, said method comprising administering to the subject an effective amount of the modified PAI-1 molecule of claim 1.

15. A method of treating tissue plasminogen activator-mediated fibrinolysis in a subject in need thereof, said method comprising administering to the subject an effective amount of the modified PAI-1 molecule of claim 1.

16. A pharmaceutical composition comprising a therapeutically effective amount of the modified PAI-1 molecule of claim 1 and a pharmaceutically acceptable carrier.

17. A modified plasminogen activator inhibitor type-1 (PAI-1) molecule comprising the amino acid sequence of SEQ ID NO:2 except for substitution by an amino acid residue that contains a sulfhydryl group at positions: (i) 31 and 97 of SEQ ID NO:2; (ii) 192 and 347 of SEQ ID NO:2; (iii) 197 and 355 of SEQ ID NO:2; (iv) 31, 97, 192, and 347 of SEQ ID NO:2; (v) 31, 97, 197, and 355 of SEQ ID NO:2; (vi) 192, 197, 347 and 355 of SEQ ID NO:2; or (vii) 31, 97, 192, 197, 347, and 355 of SEQ ID NO:2, wherein said modified PAI-1 molecule inhibits urokinase plasminogen activator.

18. A method of producing a modified plasminogen activator inhibitor type-1 (PAI-1) molecule said method comprising:
  (a) introducing into a cell a nucleic acid molecule encoding the modified PAI-1 molecule of claim 1; and
  (b) culturing the cell under conditions suitable for expression of the modified PAI-1 molecule.

19. A method of producing a modified plasminogen activator inhibitor type-1 (PAI-1) molecule said method comprising:
  (a) introducing into a cell a nucleic acid molecule encoding the modified PAI-1 molecule of claim 17; and
  (b) culturing the cell under conditions suitable for expression of the modified PAL-1 molecule.

20. The modified PAI-1 molecule of any one of claims 1, 4, or 5, wherein the half-life is an in vivo half-life.

* * * * *

SEQUENCE LISTING

<160> NUMBER OF SEQ ID NOS: 3

<210> SEQ ID NO 1
<211> LENGTH: 2876
<212> TYPE: DNA
<213> ORGANISM: Homo sapiens
<220> FEATURE:
<221> NAME/KEY: CDS
<222> LOCATION: (76)...(1281)
<223> OTHER INFORMATION: human PAI-1 plus 5' and 3' sequence

<400> SEQUENCE: 1

```
gaattcctgc agctcagcag ccgccgccag agcaggacga accgccaatc gcaaggcacc      60
tctgagaact tcagg atg cag atg tct cca gcc ctc acc tgc cta gtc ctg     111
```

```
                Met Gln Met Ser Pro Ala Leu Thr Cys Leu Val Leu
                  1               5                  10 ggc ctg gcc ctt gtc ttt ggt gaa ggg tct gct gtg cac cat ccc cca      159
Gly Leu Ala Leu Val Phe Gly Glu Gly Ser Ala Val His His Pro Pro
         15                  20                  25 tcc tac gtg gcc cac ctg gcc tca gac ttc ggg gtg agg gtg ttt cag      207
Ser Tyr Val Ala His Leu Ala Ser Asp Phe Gly Val Arg Val Phe Gln
     30                  35                  40 cag gtg gcg cag gcc tcc aag gac cgc aac gtg gtt ttc tca ccc tat      255
Gln Val Ala Gln Ala Ser Lys Asp Arg Asn Val Val Phe Ser Pro Tyr
 45                  50                  55                  60 ggg gtg gcc tcg gtg ttg gcc atg ctc cag ctg aca aca gga gga gaa      303
Gly Val Ala Ser Val Leu Ala Met Leu Gln Leu Thr Thr Gly Gly Glu
                 65                  70                  75 acc cag cag cag att caa gca gct atg gga ttc aag att gat gac aag      351
Thr Gln Gln Gln Ile Gln Ala Ala Met Gly Phe Lys Ile Asp Asp Lys
             80                  85                  90 ggc atg gcc ccc gcc ctc cgg cat ctg tac aag gag ctc atg ggg cca      399
Gly Met Ala Pro Ala Leu Arg His Leu Tyr Lys Glu Leu Met Gly Pro
         95                  100                 105 tgg aac aag gat gag atc agc acc aca gac gcg atc ttc gtc cag cgg      447
Trp Asn Lys Asp Glu Ile Ser Thr Thr Asp Ala Ile Phe Val Gln Arg
110                 115                 120 gat ctg aag ctg gtc cag ggc ttc atg ccc cac ttc ttc agg ctg ttc      495
Asp Leu Lys Leu Val Gln Gly Phe Met Pro His Phe Phe Arg Leu Phe
125                 130                 135                 140 cgg agc acg gtc aag caa gtg gac ttt tca gag gtg gag aga gcc aga      543
Arg Ser Thr Val Lys Gln Val Asp Phe Ser Glu Val Glu Arg Ala Arg
                145                 150                 155 ttc atc atc aat gac tgg gtg aag aca cac aca aaa ggt atg atc agc      591
Phe Ile Ile Asn Asp Trp Val Lys Thr His Thr Lys Gly Met Ile Ser
             160                 165                 170 aac ttg ctt ggg aaa gga gcc gtg gac cag ctg aca cgg ctg gtg ctg      639
Asn Leu Leu Gly Lys Gly Ala Val Asp Gln Leu Thr Arg Leu Val Leu
         175                 180                 185 gtg aat gcc ctc tac ttc aac ggc cag tgg aag act ccc ttc ccc gac      687
Val Asn Ala Leu Tyr Phe Asn Gly Gln Trp Lys Thr Pro Phe Pro Asp
190                 195                 200 tcc agc acc cac cgc cgc ctc ttc cac aaa tca gac ggc agc act gtc      735
Ser Ser Thr His Arg Arg Leu Phe His Lys Ser Asp Gly Ser Thr Val
205                 210                 215                 220 tct gtg ccc atg atg gct cag acc aac aag ttc aac tat act gag ttc      783
Ser Val Pro Met Met Ala Gln Thr Asn Lys Phe Asn Tyr Thr Glu Phe
                225                 230                 235 acc acg ccc gat ggc cat tac tac gac atc ctg gaa ctg ccc tac cac      831
Thr Thr Pro Asp Gly His Tyr Tyr Asp Ile Leu Glu Leu Pro Tyr His
             240                 245                 250 ggg gac acc ctc agc atg ttc att gct gcc cct tat gaa aaa gag gtg      879
Gly Asp Thr Leu Ser Met Phe Ile Ala Ala Pro Tyr Glu Lys Glu Val
         255                 260                 265 cct ctc tct gcc ctc acc aac att ctg agt gcc cag ctc atc agc cac      927
Pro Leu Ser Ala Leu Thr Asn Ile Leu Ser Ala Gln Leu Ile Ser His
270                 275                 280 tgg aaa ggc aac atg acc agg ctg ccc cgc ctc ctg gtt ctg ccc aag      975
Trp Lys Gly Asn Met Thr Arg Leu Pro Arg Leu Leu Val Leu Pro Lys
285                 290                 295                 300 ttc tcc ctg gag act gaa gtc gac ctc agg aag ccc cta gag aac ctg     1023
Phe Ser Leu Glu Thr Glu Val Asp Leu Arg Lys Pro Leu Glu Asn Leu
                305                 310                 315
```

```
gga atg acc gac atg ttc aga cag ttt cag gct gac ttc acg agt ctt    1071
Gly Met Thr Asp Met Phe Arg Gln Phe Gln Ala Asp Phe Thr Ser Leu
        320                 325                 330 tca gac caa gag cct ctc cac gtc gcg cag gcg ctg cag aaa gtg aag    1119
Ser Asp Gln Glu Pro Leu His Val Ala Gln Ala Leu Gln Lys Val Lys
            335                 340                 345 atc gag gtg aac gag agt ggc acg gtg gcc tcc tca tcc aca gct gtc    1167
Ile Glu Val Asn Glu Ser Gly Thr Val Ala Ser Ser Ser Thr Ala Val
350                 355                 360 ata gtc tca gcc cgc atg gcc ccc gag gag atc atc atg gac aga ccc    1215
Ile Val Ser Ala Arg Met Ala Pro Glu Glu Ile Ile Met Asp Arg Pro
365                 370                 375                 380 ttc ctc ttt gtg gtc cgg cac aac ccc aca gga aca gtc ctt ttc atg    1263
Phe Leu Phe Val Val Arg His Asn Pro Thr Gly Thr Val Leu Phe Met
                385                 390                 395 ggc caa gtg atg gaa ccc tgaccctggg gaaagacgcc ttcatctggg           1311
Gly Gln Val Met Glu Pro
            400 acaaaactgg agatgcatcg ggaaagaaga aactccgaag aaaagaattt tagtgttaat  1371 gactctttct gaaggaagag aagacatttg ccttttgtta aaagatggta aaccagatct  1431 gtctccaaga ccttggcctc tccttggagg acctttaggt caaactccct agtctccacc  1491 tgagaccctg ggagagaagt ttgaagcaca actcccttaa ggtctccaaa ccagacggtg  1551 acgcctgcgg gaccatctgg ggcacctgct tccacccgtc tctctgccca ctcgggtctg  1611 cagacctggt tcccactgag gcccttgca ggatggaact acggggctta caggagcttt   1671 tgtgtgcctg gtagaaacta tttctgttcc agtcacattg ccatcactct tgtactgcct  1731 gccaccgcgg aggaggctgg tgacaggcca aaggccagtg aagaaacac cctttcatct   1791 cagagtccac tgtggcactg ccacccctc cccagtacag gggtgctgca ggtggcagag   1851 tgaatgtccc ccatcatgtg gcccaactct cctggcctgg ccatctccct ccccagaaac  1911 agtgtgcatg ggttatttg gagtgtaggt gacttgttta ctcattgaag cagatttctg   1971 cttccttttta tttttatagg aatagaggaa gaaatgtcag atgcgtgccc agctcttcac  2031 cccccaatct cttggtgggg aggggtgtac ctaaatattt atcatatcct tgcccttgag  2091 tgcttgttag agagaaagag aactactaag gaaaataata ttatttaaac tcgctcctag  2151 tgtttctttg tggtctgtgt caccgtatct caggaagtcc agccacttga ctggcacaca  2211 cccctccgga catccagcgt gacggagccc acactgccac cttgtggccg cctgagaccc  2271 tcgcgccccc cgcgccccccc gcgccctct ttttcccctt gatggaaatt gaccatacaa  2331 tttcatcctc cttcaggga tcaaaggac ggagtggggg gacagagact cagatgagga   2391 cagagtggtt tccaatgtgt tcaatagatt taggagcaga aatgcaaggg gctgcatgac  2451 ctaccaggac agaactttcc ccaattacag ggtgactcac agccgcattg gtgactcact  2511 tcaatgtgtc atttccggct gctgtgtgtg agcagtggac acgtgagggg ggggtgggtg  2571 agagagacag gcagctcgga ttcaactacc ttagataata tttctgaaaa cctaccagcc  2631 agagggtagg gcacaaagat ggatgtaatg cactttggga ggccaaggcg ggaggattgc  2691 ttgagcccag gagttcaaga ccagcctggg caacatacca gaccccgt ctctttaaaa   2751 atatatatat tttaaatata cttaaatata tatttctaat atctttaaat atatatatat  2811 atttttaaaga ccaatttatg ggagaattgc acacagatgt gaaatgaatg taatctaata  2871 gaagc                                                              2876
```

```
<210> SEQ ID NO 2
<211> LENGTH: 402
<212> TYPE: PRT
<213> ORGANISM: Homo sapiens
<220> FEATURE:
<223> OTHER INFORMATION: human PAI-1 amino acid sequence, including
      signal peptide

<400> SEQUENCE: 2

Met Gln Met Ser Pro Ala Leu Thr Cys Leu Val Leu Gly Leu Ala Leu
 1               5                  10                  15

Val Phe Gly Glu Gly Ser Ala Val His His Pro Pro Ser Tyr Val Ala
            20                  25                  30

His Leu Ala Ser Asp Phe Gly Val Arg Val Phe Gln Gln Val Ala Gln
        35                  40                  45

Ala Ser Lys Asp Arg Asn Val Val Phe Ser Pro Tyr Gly Val Ala Ser
    50                  55                  60

Val Leu Ala Met Leu Gln Leu Thr Thr Gly Gly Glu Thr Gln Gln Gln
65                  70                  75                  80

Ile Gln Ala Ala Met Gly Phe Lys Ile Asp Asp Lys Gly Met Ala Pro
                85                  90                  95

Ala Leu Arg His Leu Tyr Lys Glu Leu Met Gly Pro Trp Asn Lys Asp
            100                 105                 110

Glu Ile Ser Thr Thr Asp Ala Ile Phe Val Gln Arg Asp Leu Lys Leu
        115                 120                 125

Val Gln Gly Phe Met Pro His Phe Phe Arg Leu Phe Arg Ser Thr Val
    130                 135                 140

Lys Gln Val Asp Phe Ser Glu Val Glu Arg Ala Arg Phe Ile Ile Asn
145                 150                 155                 160

Asp Trp Val Lys Thr His Thr Lys Gly Met Ile Ser Asn Leu Leu Gly
                165                 170                 175

Lys Gly Ala Val Asp Gln Leu Thr Arg Leu Val Leu Val Asn Ala Leu
            180                 185                 190

Tyr Phe Asn Gly Gln Trp Lys Thr Pro Phe Pro Asp Ser Ser Thr His
        195                 200                 205

Arg Arg Leu Phe His Lys Ser Asp Gly Ser Thr Val Ser Val Pro Met
    210                 215                 220

Met Ala Gln Thr Asn Lys Phe Asn Tyr Thr Glu Phe Thr Thr Pro Asp
225                 230                 235                 240

Gly His Tyr Tyr Asp Ile Leu Glu Leu Pro Tyr His Gly Asp Thr Leu
                245                 250                 255

Ser Met Phe Ile Ala Ala Pro Tyr Glu Lys Glu Val Pro Leu Ser Ala
            260                 265                 270

Leu Thr Asn Ile Leu Ser Ala Gln Leu Ile Ser His Trp Lys Gly Asn
        275                 280                 285

Met Thr Arg Leu Pro Arg Leu Leu Val Leu Pro Lys Phe Ser Leu Glu
    290                 295                 300

Thr Glu Val Asp Leu Arg Lys Pro Leu Glu Asn Leu Gly Met Thr Asp
305                 310                 315                 320

Met Phe Arg Gln Phe Gln Ala Asp Phe Thr Ser Leu Ser Asp Gln Glu
                325                 330                 335

Pro Leu His Val Ala Gln Ala Leu Gln Lys Val Lys Ile Glu Val Asn
            340                 345                 350

Glu Ser Gly Thr Val Ala Ser Ser Ser Thr Ala Val Ile Val Ser Ala
        355                 360                 365
```

```
Arg Met Ala Pro Glu Ile Ile Met Asp Arg Pro Phe Leu Phe Val
    370             375             380

Val Arg His Asn Pro Thr Gly Thr Val Leu Phe Met Gly Gln Val Met
385             390             395                 400

Glu Pro

<210> SEQ ID NO 3
<211> LENGTH: 379
<212> TYPE: PRT
<213> ORGANISM: Homo sapiens
<220> FEATURE:
<223> OTHER INFORMATION: human PAI-1 mature amino acid sequence

<400> SEQUENCE: 3

Val His His Pro Pro Ser Tyr Val Ala His Leu Ala Ser Asp Phe Gly
  1               5                  10                  15

Val Arg Val Phe Gln Gln Val Ala Gln Ala Ser Lys Asp Arg Asn Val
                 20                  25                  30

Val Phe Ser Pro Tyr Gly Val Ala Ser Val Leu Ala Met Leu Gln Leu
             35                  40                  45

Thr Thr Gly Gly Glu Thr Gln Gln Gln Ile Gln Ala Ala Met Gly Phe
 50                  55                  60

Lys Ile Asp Asp Lys Gly Met Ala Pro Ala Leu Arg His Leu Tyr Lys
 65                  70                  75                  80

Glu Leu Met Gly Pro Trp Asn Lys Asp Glu Ile Ser Thr Thr Asp Ala
                 85                  90                  95

Ile Phe Val Gln Arg Asp Leu Lys Leu Val Gln Gly Phe Met Pro His
                100                 105                 110

Phe Phe Arg Leu Phe Arg Ser Thr Val Lys Gln Val Asp Phe Ser Glu
            115                 120                 125

Val Glu Arg Ala Arg Phe Ile Ile Asn Asp Trp Val Lys Thr His Thr
130                 135                 140

Lys Gly Met Ile Ser Asn Leu Leu Gly Lys Gly Ala Val Asp Gln Leu
145                 150                 155                 160

Thr Arg Leu Val Leu Val Asn Ala Leu Tyr Phe Asn Gly Gln Trp Lys
                165                 170                 175

Thr Pro Phe Pro Asp Ser Ser Thr His Arg Arg Leu Phe His Lys Ser
            180                 185                 190

Asp Gly Ser Thr Val Ser Val Pro Met Met Ala Gln Thr Asn Lys Phe
        195                 200                 205

Asn Tyr Thr Glu Phe Thr Thr Pro Asp Gly His Tyr Tyr Asp Ile Leu
    210                 215                 220

Glu Leu Pro Tyr His Gly Asp Thr Leu Ser Met Phe Ile Ala Ala Pro
225                 230                 235                 240

Tyr Glu Lys Glu Val Pro Leu Ser Ala Leu Thr Asn Ile Leu Ser Ala
                245                 250                 255

Gln Leu Ile Ser His Trp Lys Gly Asn Met Thr Arg Leu Pro Arg Leu
            260                 265                 270

Leu Val Leu Pro Lys Phe Ser Leu Glu Thr Glu Val Asp Leu Arg Lys
        275                 280                 285

Pro Leu Glu Asn Leu Gly Met Thr Asp Met Phe Arg Gln Phe Gln Ala
    290                 295                 300

Asp Phe Thr Ser Leu Ser Asp Gln Glu Pro Leu His Val Ala Gln Ala
305                 310                 315                 320

Leu Gln Lys Val Lys Ile Glu Val Asn Glu Ser Gly Thr Val Ala Ser
```

-continued

```
                    325                 330                 335
Ser Ser Thr Ala Val Ile Val Ser Ala Arg Met Ala Pro Glu Glu Ile
            340                 345                 350
Ile Met Asp Arg Pro Phe Leu Phe Val Val Arg His Asn Pro Thr Gly
            355                 360                 365
Thr Val Leu Phe Met Gly Gln Val Met Glu Pro
    370                 375
```